(12) United States Patent
Suzuki

(10) Patent No.: US 11,930,998 B2
(45) Date of Patent: Mar. 19, 2024

(54) VENT CONTROL VALVE FOR ENDOSCOPE AND ENDOSCOPE

(71) Applicant: OLYMPUS CORPORATION, Tokyo (JP)

(72) Inventor: Masanori Suzuki, Tama (JP)

(73) Assignee: OLYMPUS CORPORATION, Tokyo (JP)

(*) Notice: Subject to any disclaimer, the term of this patent is extended or adjusted under 35 U.S.C. 154(b) by 762 days.

(21) Appl. No.: 17/124,958

(22) Filed: Dec. 17, 2020

(65) Prior Publication Data
US 2021/0100432 A1 Apr. 8, 2021

Related U.S. Application Data

(63) Continuation of application No. PCT/JP2018/031442, filed on Aug. 24, 2018.

(51) Int. Cl.
*A61B 1/00* (2006.01)
(52) U.S. Cl.
CPC ...... *A61B 1/00068* (2013.01); *A61B 1/00073* (2013.01)
(58) Field of Classification Search
CPC .... A61B 1/00068; A61B 1/015; A61M 39/22; A61M 39/223
See application file for complete search history.

(56) References Cited

U.S. PATENT DOCUMENTS

2006/0041190 A1\* 2/2006 Sato .................. A61B 1/00068
600/159
2015/0216393 A1\* 8/2015 Toyoda .............. A61B 1/00068
600/159

FOREIGN PATENT DOCUMENTS

| JP | H05-253168 A | 10/1993 |
|---|---|---|
| JP | H08-086966 A | 4/1996 |
| JP | H09-051872 A | 2/1997 |
| JP | 2000-102508 A | 4/2000 |
| JP | 2000-157484 A | 6/2000 |
| JP | 2004-222888 A | 8/2004 |
| JP | 2009-060996 A | 3/2009 |
| JP | 2015-029649 A | 2/2015 |
| JP | 2015-053978 A | 3/2015 |

OTHER PUBLICATIONS

International Search Report dated Oct. 23, 2018 issued in PCT/JP2018/031442.

\* cited by examiner

*Primary Examiner* — Alexandra L Newton
(74) *Attorney, Agent, or Firm* — Scully, Scott, Murphy & Presser, P.C.

(57) ABSTRACT

A vent control valve for an endoscope includes a shaft body including a pin fixing portion, and a vent hole including a long hole with an opening provided in one end surface, and a long hole communication hole configured to cause an outside and an inside of the long hole to communicate with each other, a tubular member including a shaft body hole configured to house the shaft body, and a cam groove in which the cam pin is disposed, a rotational member including a tubular member hole where the tubular member is disposed, a cam pin groove where the cam pin is disposed, and a plurality of engaging holes, and a cylindrical housing member including an attaching portion fixedly provided in a casing through-hole, and a housing hole communicating with the internal space.

9 Claims, 21 Drawing Sheets

VENT CONTROL VALVE FOR ENDOSCOPE AND ENDOSCOPE

CROSS REFERENCE TO RELATED APPLICATION

This application is a continuation application of PCT/JP2018/031442 filed on Aug. 24, 2018, the entire contents of which are incorporated herein by this reference.

BACKGROUND OF THE INVENTION

1. Field of the Invention

The present invention relates to a vent control valve for an endoscope with a characteristic vent pipe sleeve, and an endoscope including an adaptor configured to be connected to the vent pipe sleeve.

2. Description of the Related Art

A medical endoscope generally has an elongated insertion portion configured to be inserted into a body cavity, and an operation portion provided at a proximal end side of the insertion portion.

In recent years, a medical endoscope is cleaned and subjected to autoclave sterilization after use. In autoclave sterilization, the endoscope is left in a chamber. The endoscope in the chamber is subjected to autoclave sterilization treatment through a pre-vacuum step, a high-pressure steam sterilization step, and a drying step. After autoclave sterilization is finished, the endoscope is left in the atmosphere.

Japanese Patent Application Laid-Open Publication No. 08-86966 discloses an inner pressure adjustment apparatus for an endoscope that can place an endoscope in a vacuum sterilization room so that a soft coating portion does not rupture, and can also make the endoscope usable normally without any problem by automatically bringing the internal pressure of the endoscope to atmospheric pressure after vacuum sterilization.

Japanese Patent Application Laid-Open Publication No. 2015-029649 discloses an endoscope that prevents occurrence of a trouble due to an erroneous operation of a vent valve capable of switching an internal space and an external space of an endoscope to a cutoff state and a communication state. The endoscope includes a check valve unit and a pressure return valve unit in a partition wall portion of an exterior member partitioning the internal space and the external space.

SUMMARY OF THE INVENTION

A vent control valve for an endoscope of one aspect of the present invention includes a shaft body including a pin fixing portion which is provided in an outer peripheral surface and to which one end of a cam pin is fixed, and a vent hole including a long hole set to a predetermined depth with an opening provided in one end surface, and a long hole communication hole including a vent opening formed in the outer peripheral surface and configured to cause an outside and an inside of the long hole to communicate with each other through the vent opening, a tubular member including a shaft body hole that is a through-hole configured to house the shaft body rotatably around an axis and movably in an axial direction and extending in a longitudinal direction along a center axis, and a cam groove in which another end portion of the cam pin is slidably disposed, on an outer peripheral portion, a rotational member including a tubular member hole where the tubular member is disposed rotatably around an axis, an elongated cam pin groove where the other end portion of the cam pin protruded outward from the cam groove is disposed, the cam pin groove extending in a longitudinal direction along a center axis from one end surface and causing the tubular member hole and an outside to communicate with each other, and a plurality of engaging holes provided at predetermined positions of another end surface, and a cylindrical housing member including an attaching portion fixedly provided in a casing through-hole causing an internal space of a casing configuring the endoscope and an outside to communicate with each other, and a housing hole including a bottom surface opening of a housing through-hole communicating with the internal space, in a bottom surface, and configured to house the rotational member.

An endoscope of one aspect of the present invention includes a vent control valve, and the vent control valve includes a shaft body including a pin fixing portion which is provided in an outer peripheral surface and to which one end of a cam pin is fixed, and a vent hole including a long hole set to a predetermined depth with an opening provided in one end surface and a long hole communication hole including a vent opening formed in the outer peripheral surface and configured to cause an outside and an inside of the long hole to communicate with each other through the vent opening, a tubular member including a shaft body hole that is a through-hole configured to house the shaft body rotatably around an axis and movably in an axial direction and extending in a longitudinal direction along a center axis, and a cam groove in which another end portion of the cam pin is slidably disposed, on an outer peripheral portion, a rotational member including a tubular member hole where the tubular member is disposed rotatably around an axis, an elongated cam pin groove where the other end portion of the cam pin protruded outward from the cam groove is disposed, the cam pin groove extending in a longitudinal direction along a center axis from one end surface and causing the tubular member hole and an outside to communicate with each other, and a plurality of engaging holes provided at predetermined positions of another end surface, and a cylindrical housing member including an attaching portion fixedly provided in a casing through-hole causing an internal space of a casing configuring the endoscope and an outside to communicate with each other, and a housing hole including a bottom surface opening of a housing through-hole communicating with the internal space, in a bottom surface, and configured to house the rotational member.

DETAILED DESCRIPTION OF THE PREFERRED EMBODIMENT

Figure 1:
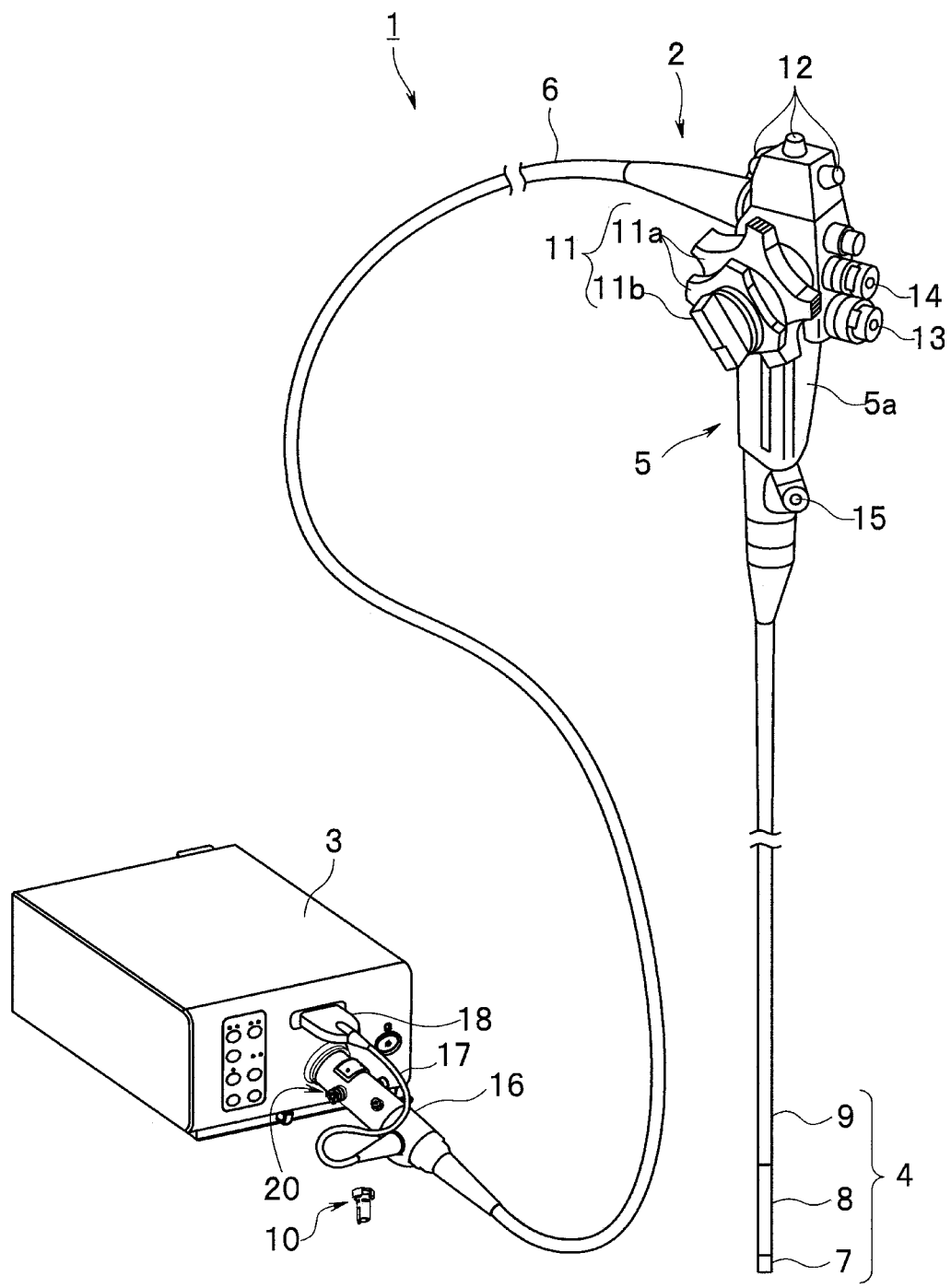
FIG. 1 is a view explaining an endoscope apparatus including an endoscope including a vent pipe sleeve in an endoscope connector, and a sterilization cap attachable to and detachable from the vent pipe sleeve.

Hereinafter, an embodiment of the present invention will be described with reference to the drawings.

Note that in respective drawings that are used in the following explanation, a scale may differ for each of components so that the respective components have such sizes that the respective components are recognizable on the drawings. In other words, the present invention is not limited to only numbers and quantities of the components, shapes of the components, ratios of sizes of the components, and relative positional relationship of the respective components that are illustrated in the drawings.

As illustrated in FIG. 1, an endoscope apparatus 1 is configured by having an endoscope 2, a camera control unit (hereinafter, described as CCU) 3, for example, that is an external apparatus, a monitor (not illustrated), and an adaptor 10.

The adaptor 10 is an adaptor for sterilization having a check valve unit.

The endoscope 2 has an insertion portion 4, an operation portion 5, and a universal cord 6. The insertion portion 4 is an elongated member of a long length configured to be inserted into an observation target site. In the insertion portion 4, a distal end portion 7, a bending portion 8, and a flexible tube portion 9 are continuously provided in order from a distal end side.

The operation portion 5 includes a grasping portion 5a, and the grasping portion 5a is connected to a proximal end portion of the insertion portion 4. In the operation portion 5, a bending operation portion 11, various switches 12, an air/water feeding button 13, a suction button 14 and the like are provided.

The bending operation portion 11 has an up-down operation knob 11a, and a left-right operation knob 11b, for example, for performing a bending operation of the bending portion 8. The switches 12 are, for example, a release switch, a freeze switch, and an observation mode changeover switch for performing switching of normal observation and fluorescence observation. Note that reference sign 15 denotes a treatment instrument insertion port.

The universal cord 6 extends from a side portion of the operation portion 5. An endoscope connector 16 that is one of casings configuring the endoscope is provided at an end portion of the universal cord 6.

A signal transmission cable 17 is extended from the endoscope connector 16. An electric connector 18 that is one of the casings of the endoscope and attachable to and detachable from the CCU3 is provided at a cable end portion.

In the present embodiment, a vent pipe sleeve 20 is provided to protrude from an outer surface (see reference sign 16o in FIG. 2) of the endoscope connector 16.

Note that the vent pipe sleeve 20 may be provided to protrude from an outer surface of the operation portion 5 that is one of the casings of the endoscope. The endoscope may be a portable endoscope.

Figure 2:
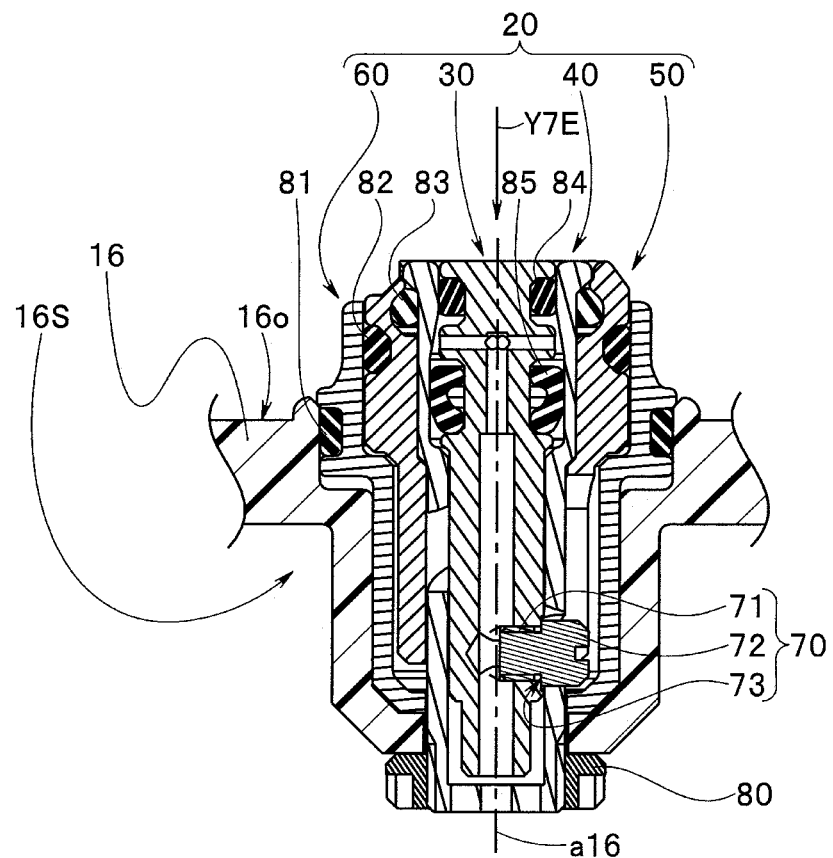
FIG. 2 is a view explaining the vent pipe sleeve of the endoscope connector.

As illustrated in FIG. 2, in the endoscope connector 16, a stepped hole for pipe sleeve (hereinafter, described as a pipe sleeve hole) 16h is formed. The pipe sleeve hole 16h is formed in a partition wall partitioning an outside and an internal space. The pipe sleeve hole 16h is a casing through-hole configured to cause the outside of the endoscope connector 16 and a connector space 16S that is the internal space to communicate with each other.

In the endoscope connector 16, a vent pipe sleeve 20 is provided in the pipe sleeve hole 16h. In the vent pipe sleeve 20, a shaft body 30, a tubular member 40, a rotational member 50, and a housing member 60 are disposed. The shaft body 30, the tubular member 40, the rotational member 50, and the housing member 60 that are disposed in the pipe sleeve hole 16h are fixedly provided by a fixing nut 80 to be watertight.

Reference sign a16 denotes a hole center axis of the pipe sleeve hole 16h. A center axis of the shaft body 30 disposed in the pipe sleeve hole 16h, a center axis of the tubular member 40, a center axis of the rotational member 50, and a center axis of the housing member 60 substantially correspond to the hole center axis a16.

Reference sign 81 denotes a first watertight member, and a so-called O-shaped ring with a circular sectional shape. The first watertight member 81 is described as a first O-shaped ring 81. The first O-shaped ring 81 maintains watertightness between the pipe sleeve hole 16h and the housing member 60. Reference sign 82 denotes a second watertight member, and a so-called O-shaped ring with a circular sectional shape. The second watertight member is described as a second O-shaped ring 82. The second O-shaped ring 82 maintains watertightness between the housing member 60 and the rotational member 50.

Reference sign 83 denotes a third watertight member, and a so-called O-shaped ring with a circular sectional shape. The third watertight member is described as a third O-shaped ring 83. The third O-shaped ring 83 maintains watertightness between the rotational member 50 and the tubular member 40. Reference sign 84 denotes a fourth watertight member, and a so-called O-shaped ring with a circular sectional shape. The fourth watertight member 84 is described as a fourth O-shaped ring 84. The fourth O-shaped ring 84 maintains watertightness between the tubular member 40 and the shaft body 30. Reference sign 85 denotes a fifth watertight member, and a so-called O-shaped ring having a substantially rectangular sectional shape different from the aforementioned circular sectional shape, and having a relief groove on an inner surface side. The fifth watertight member is described as a fifth O-shaped ring 85. The fifth O-shaped ring 85 also maintains watertightness between the tubular member 40 and the shaft body 30.

Reference sign 70 denotes a rod-shaped cam pin.

Figure 3A:
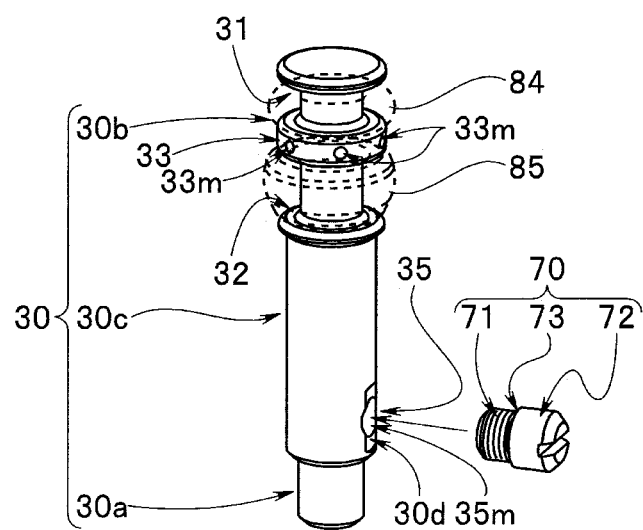
FIG. 3A is a perspective view explaining a shaft body and a cam pin.
Figure 3B:
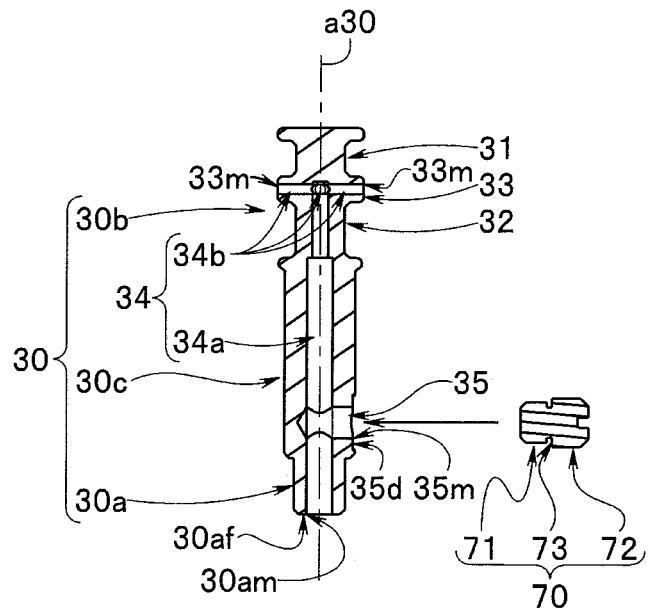
FIG. 3B is a sectional view in a longitudinal direction explaining the shaft body and the cam pin.

The cam pin 70 will be described with reference to FIG. 2, FIG. 3A and FIG. 3B.

The cam pin 70 is rod-shaped, and has a thin pin portion 71, a thick pin portion 72, and a stepped surface 73. The thin pin portion 71 that is one end portion of the cam pin 70 is fixed to the shaft body 30. A male thread is cut on an outer peripheral surface of the thin pin portion 71. The thick pin portion 72 is the other end portion of the thin pin portion 71.

The shaft body 30 will be described with reference to FIG. 3A and FIG. 3B.

The shaft body 30 is a stepped circular column. The shaft body 30 has a small diameter portion 30a, a large diameter portion 30b, and a middle portion 30c. On the large diameter portion 30b of the shaft body 30, a first circumferential groove 31 and a second circumferential groove 32 are formed. The second circumferential groove 32 is provided on a middle portion 30c side, and the fifth O-shaped ring 85 is disposed. The fourth O-shaped ring 84 is disposed in the first circumferential groove 31.

A boundary surface 33 is between the first circumferential groove 31 and the second circumferential groove 32. A plurality of vent openings 33m are formed in the boundary surface 33.

Reference sign 34 denotes a vent hole. The vent hole 34 includes a long hole 34a and a plurality of long hole communication holes 34b.

The long hole 34a is an elongated bottomed hole extending along a longitudinal axis a30 of the shaft body 30. The long hole 34a is, for example, a stepped hole set to a predetermined depth and having an opening 30am in one end surface 30af.

The long hole communication holes 34b are formed orthogonally to the longitudinal axis a30, for example, and communicate with an inside of the long hole 33a. The vent openings 33m are openings on an outer side of the long hole communication holes 34b. The outside and the long hole 34a communicate with each other by the long hole communication holes 34b.

In the present embodiment, six of the vent openings 33m are provided in the boundary surface 33. A number of vent openings 33m is set as six to prevent all of the vent openings 33m from being closed with foreign matter. Note that in order to prevent closure with foreign matter, six or more vent openings 33m may be provided.

Note that an inside diameter of the long hole 34a is set to a larger diameter than an inside diameter of the long hole communication hole 34b. Accordingly, foreign matter entering the long hole communication hole 34b from the vent opening 33m moves into the long hole 34a by passing through the long hole communication hole 34b. In other words, foreign matter is prevented from staying in the long hole communication hole 34b.

In the above explanation, the long hole communication holes 34b are described as being orthogonal to the longitudinal axis a30. However, the long hole communication holes 34b can communicate with the inside of the long hole 33a.

Reference sign 35 denotes a pin fixing portion 35. The pin fixing portion 35 is a through-hole causing the outside and the long hole 34a to communicate with each other, and has a female thread cut. The pin fixing portion 35 is provided in a predetermined position of the middle portion 30c, and has a thread opening 35m on an outer peripheral surface of the middle portion 30c.

The thin pin portion 71 of the cam pin 70 is fixedly provided in the pin fixing portion 35 by screwing. The stepped surface 73 abuts on an attaching surface 30d of the middle portion 30c, and thereby a protruding amount of the thick pin portion 72 is defined.

Figure 4A:
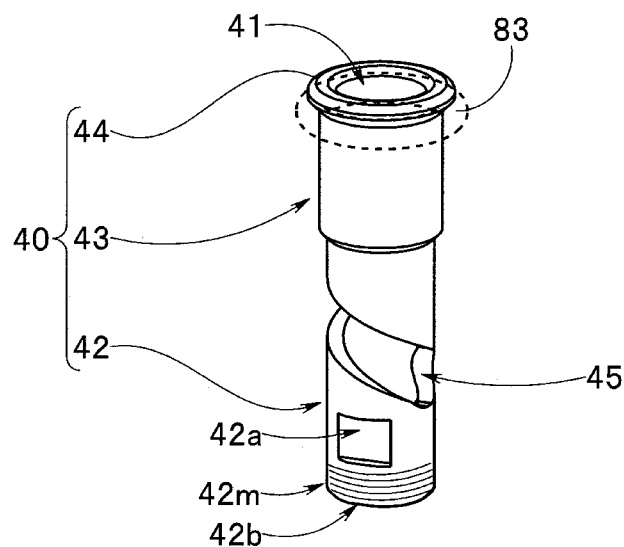
FIG. 4A is a perspective view explaining a tubular member.
Figure 4B:
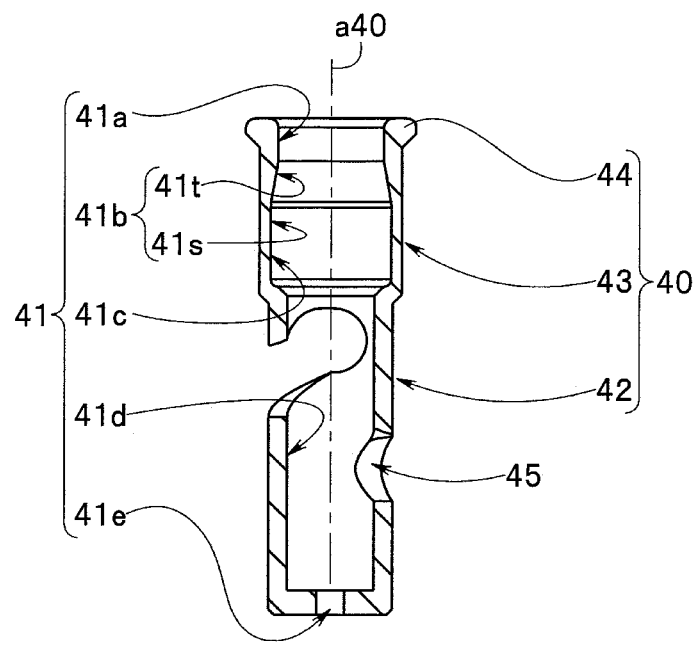
FIG. 4B is a sectional view in a longitudinal direction explaining the tubular member.

The tubular member 40 will be described with reference to FIG. 4A and FIG. 4B.

The tubular member 40 is a pipe having a through-hole in a center. The central through-hole is a shaft body hole 41 extending in a longitudinal direction along a center axis a40 of the tubular member 40.

The tubular member 40 includes a cam forming portion 42 having a small diameter, and a main body portion 43 having a larger diameter than the cam forming portion 42.

An outer flange 44 is provided on an end surface of an outer peripheral portion of the main body portion 43. The outer flange 44 has a function as a stopper that prevents the third O-shaped ring 83 from falling outward.

A spiral cam groove 45 is formed on an outer peripheral portion of the cam forming portion 42. The cam groove 45 communicates with the outside and the shaft body hole 41. The thick pin portion 72 of the cam pin 70 protruding from the shaft body 30 is slidably disposed in the cam groove 45.

Reference sign 42a denotes a defining surface, reference sign 42b denotes a forming portion end surface, and reference sign 42m denotes a male thread portion. The male thread portion 42m is formed on a forming portion end surface 42b side of the cam forming portion 42. The defining surface 42a is a flat surface formed with a predetermined area between the cam groove 45 and the male thread portion 42m.

The defining surface 42a is disposed to abut on a positioning surface (refer to reference sign 60s in FIG. 6C) provided in the pipe sleeve hole 16h. As a result, an orientation of the tubular member 40 in the pipe sleeve hole 16h is restricted to a predetermined orientation. The fixing nut 80 is screwed onto the male thread portion 42m.

The shaft body 30 is housed in the aforementioned shaft body hole 41. The shaft body 30 is rotatable around the axis in the shaft body hole 41, and is movable in an axial direction.

The shaft body hole 41 includes a watertightness maintaining portion 41a, a fifth O-shaped ring disposing portion 41b, a relief portion 41c, a sliding portion 41d, and a vent hole 41e, in order from an outer flange 44 side.

The small diameter portion 30a, and the middle portion 30c of the shaft body 30 are disposed in the sliding portion 41d. Here, an outside diameter of the middle portion 30c and an inside diameter of the sliding portion 41d are set to a predetermined fit.

The large diameter portion 30b of the shaft body 30 is disposed in the watertightness maintaining portion 41a, in the fifth O-shaped ring disposing portion 41b, and the relief portion 41c.

The fourth O-shaped ring 84 provided in the shaft body 30 closely contacts the watertightness maintaining portion 41a to maintain watertightness. The fifth O-shaped ring 85 provided in the shaft body 30 also closely contacts the watertightness maintaining portion 41a to maintain watertightness.

The fifth O-shaped ring disposing portion 41b has a taper surface 41t and a straight hole 41s. The fifth O-shaped ring 85 is disposed to abut on the straight hole 41s and closely contact the taper surface 41t.

The relief portion 41c is an extension portion of an inner surface of the straight hole 41s.

The vent hole 41e is a through-hole causing an inside of the shaft body hole 41 and the outside to communicate with each other.

Figure 5A:
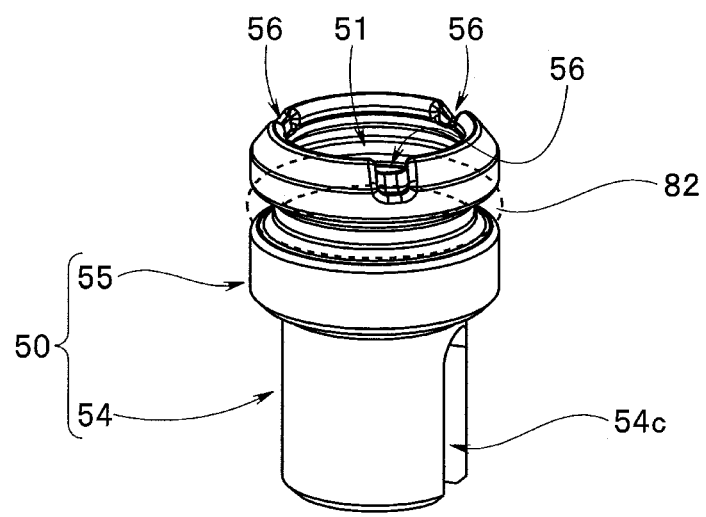
FIG. 5A is a perspective view explaining a rotational member.
Figure 5B:
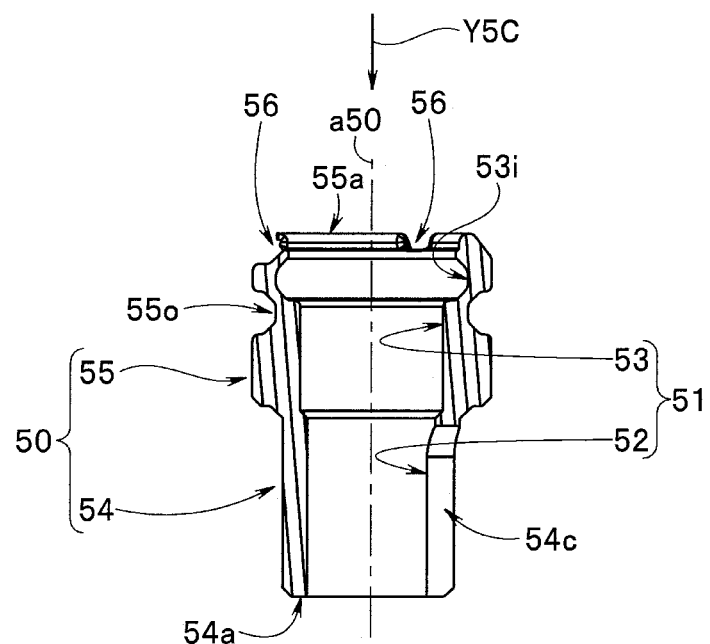
FIG. 5B is a sectional view in a longitudinal direction explaining the rotational member.
Figure 5C:
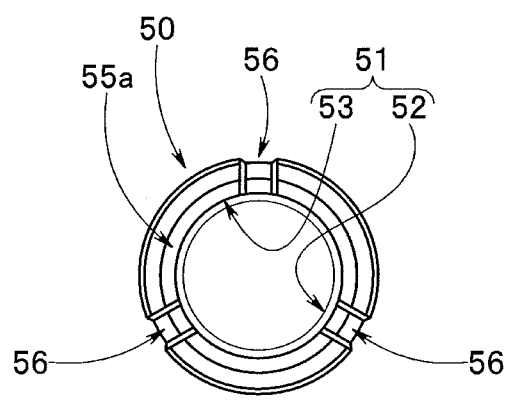
FIG. 5C is a view of the rotational member seen in an arrow Y5C direction in FIG. 5B.

The rotational member 50 will be described with reference to FIG. 5A, FIG. 5B, and FIG. 5C.

The rotational member 50 has a through-hole in a center. The central through-hole is a tubular member hole 51 extending in a longitudinal direction along a center axis a50 of the rotational member 50. The tubular member 40 is disposed in the tubular member hole 51.

The rotational member 50 includes a cam pin support portion 54, and a rotational main body 55. On the cam pin support portion 54, a cam pin groove 54c is formed in a predetermined position.

The cam pin groove 54c extends in a longitudinal direction along a center axis a50 from a cam support portion end surface 54a that is an end surface on one side of the rotational member 50. The thick pin portion 72 of the cam pin 70 is disposed in the cam pin groove 54c. A width of the cam pin groove 54c is set to be larger than a diameter of the thick pin portion 72 by a predetermined tolerance.

An outer circumferential groove 55o is formed on an outer peripheral surface of the rotational main body 55. The second O-shaped ring 82 is disposed in the outer circumferential groove 55o.

A plurality of recessed portions 56 are formed on a main body end surface 55a of the rotational main body 55 that is an end surface on the other side of the rotational member 50. Locking portions described later of the adaptor 10 are engaged with the plurality of recessed portions 56.

Three of the plurality of recessed portions 56 are provided at equal intervals in a circumferential direction, for example. The three recessed portions 56 are engaging holes with which the locking portions of the adaptor 10 are engaged. Hereinafter, the recessed portion 56 will be described as the engaging hole 56.

Forming positions of the three engaging holes 56 are set in consideration of cleanability.

The aforementioned tubular member hole 51 has a cam forming portion hole 52, and a main body portion hole 53. The main body portion 43 is housed in the main body portion hole 53, and the cam forming portion 42 is disposed in the cam forming portion hole 52. An opening communicating with the cam forming portion hole 52 is formed in a bottom surface of the main body portion hole 53.

An inside diameter of the main body portion hole 53 and an outside diameter of the main body portion 43 are set to a predetermined fit, and an inside diameter of the cam forming portion hole 52 and an outside diameter of the cam forming portion 42 are set to a predetermined fit.

Reference sign 53i denotes an inner circumferential groove. The inner circumferential groove 53i is formed on an inner surface of the main body portion hole 53. The third O-shaped ring 83 is disposed in the inner circumferential groove 53i.

Figure 6A:
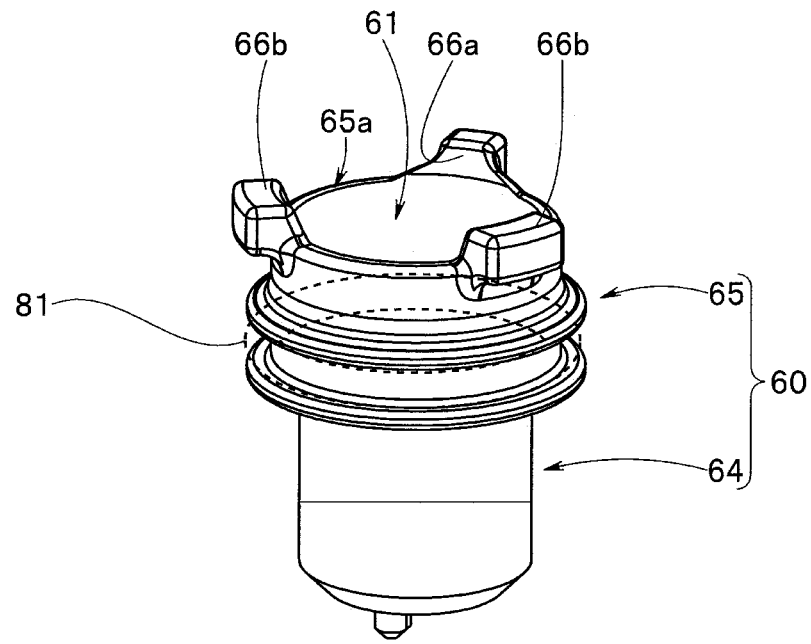
FIG. 6A is a perspective view explaining a housing member.
Figure 6B:
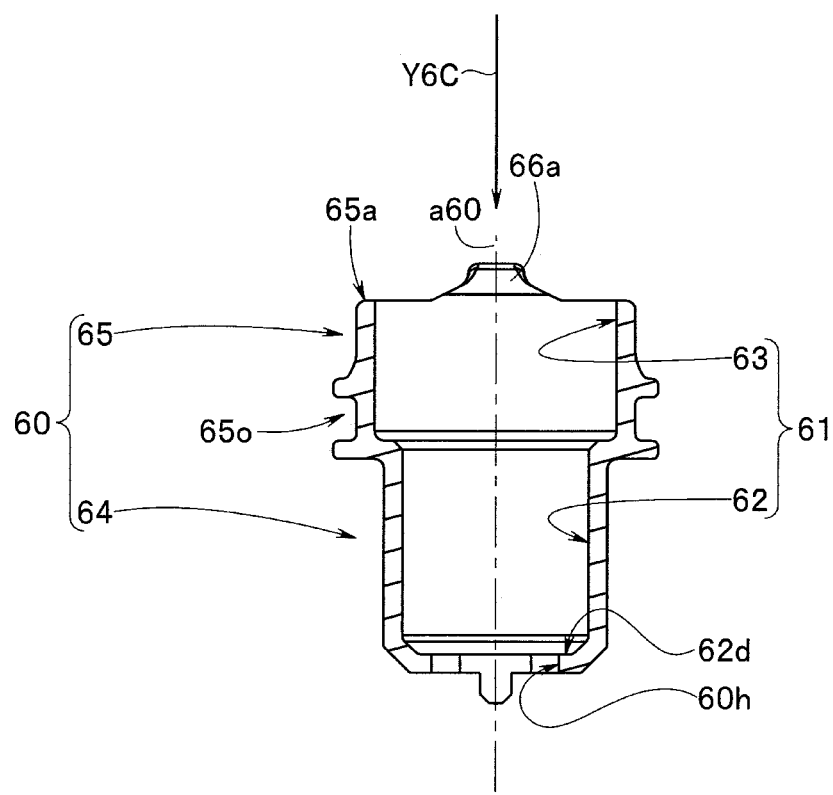
FIG. 6B is a sectional view in a longitudinal direction explaining the housing member.
Figure 6C:
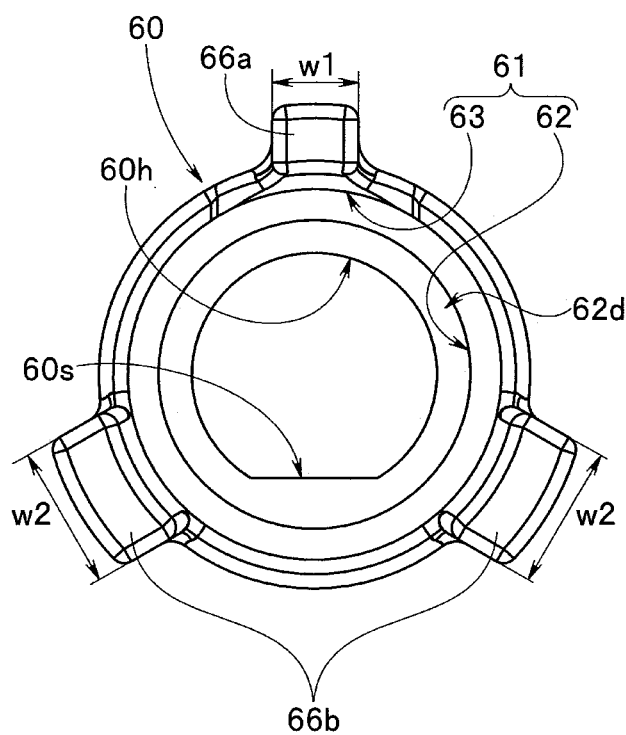
FIG. 6C is a view of the housing member seen in an arrow Y6C direction in FIG. 6B.

The housing member 60 will be described with reference to FIG. 6A, FIG. 6B, and FIG. 6C.

The housing member 60 has, in a center, a stepped housing hole 61 extending in the longitudinal direction along a center axis a60. The rotational member 50 is housed in the housing hole 61.

The housing member 60 includes a connector attaching portion 64, and an adaptor attaching portion 65.

The connector attaching portion 64 is placed in the pipe sleeve hole 16h. A part of the adaptor attaching portion 65 is placed in the pipe sleeve hole 16h, and the other part is exposed to outside from the pipe sleeve hole 16h.

An outer circumferential groove 65o is formed on the adaptor attaching portion 65 placed in the pipe sleeve hole 16h. The first O-shaped ring 81 is disposed in the outer circumferential groove 65o.

At a peripheral end portion 65a of the adaptor attaching portion 65, three protruding portions 66 protruding outward by a predetermined amount are provided at predetermined positions. The three protruding portions 66 are provided at equal intervals in a circumferential direction, for example.

The three protruding portions 66 each includes a circular arc with a width set to a predetermined width. The present embodiment has a first protruding portion 66a having a first circular arc with a width set to w1, and two second protruding portions 66b each having a second circular arc with a width set to w2. The width w2 is set to be wider than the width w1.

Ridgelines of the respective protruding portions 66a and 66b are machined into curved surfaces.

The aforementioned housing hole 61 has a support portion housing hole 62, and a main body housing hole 63. The rotational main body 55 is disposed in the main body housing hole 63. The cam pin support portion 54 is housed in the support portion housing hole 62.

On a bottom surface 62d of the support portion housing hole 62, a bottom surface opening of a housing through-hole 60h communicating with an outside is formed. The bottom surface opening is a positioning hole (hereinafter, described as a tubular member positioning hole 60h) for positioning the cam forming portion 42 of the tubular member 40 disposed in the housing through-hole 60h. A straight portion 60s corresponding to the defining surface 42a of the cam forming portion 42 is formed in the tubular member positioning hole 60h.

Assembly of the shaft body 30, the tubular member 40, the rotational member 50, and the housing member 60, and the vent pipe sleeve 20 of the endoscope connector will be described with reference to FIG. 7A to FIG. 7E.

Figure 7A:
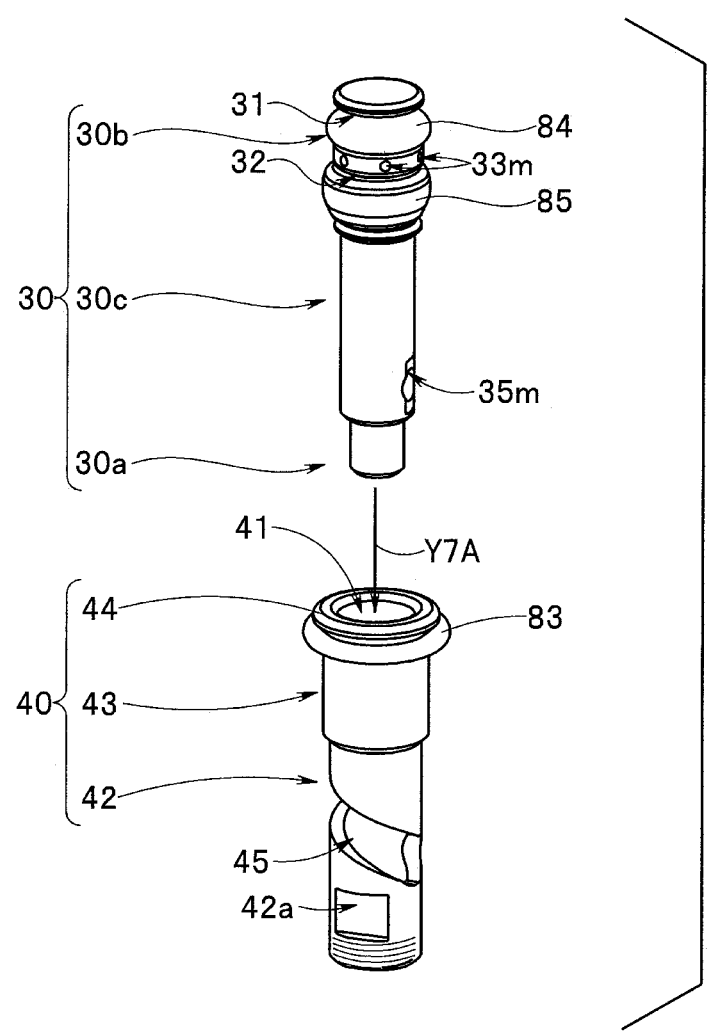
FIG. 7A is a view explaining a relationship between the shaft body and the tubular member.

An operator firstly places the fourth O-shaped ring 84 in the first circumferential groove 31 formed on the large diameter portion 30b of the shaft body 30 as illustrated in FIG. 7A, and places the fifth O-shaped ring 85 in the second circumferential groove 32. The third O-shaped ring 83 is disposed on the main body portion 43 of the tubular member 40.

Figure 7B:
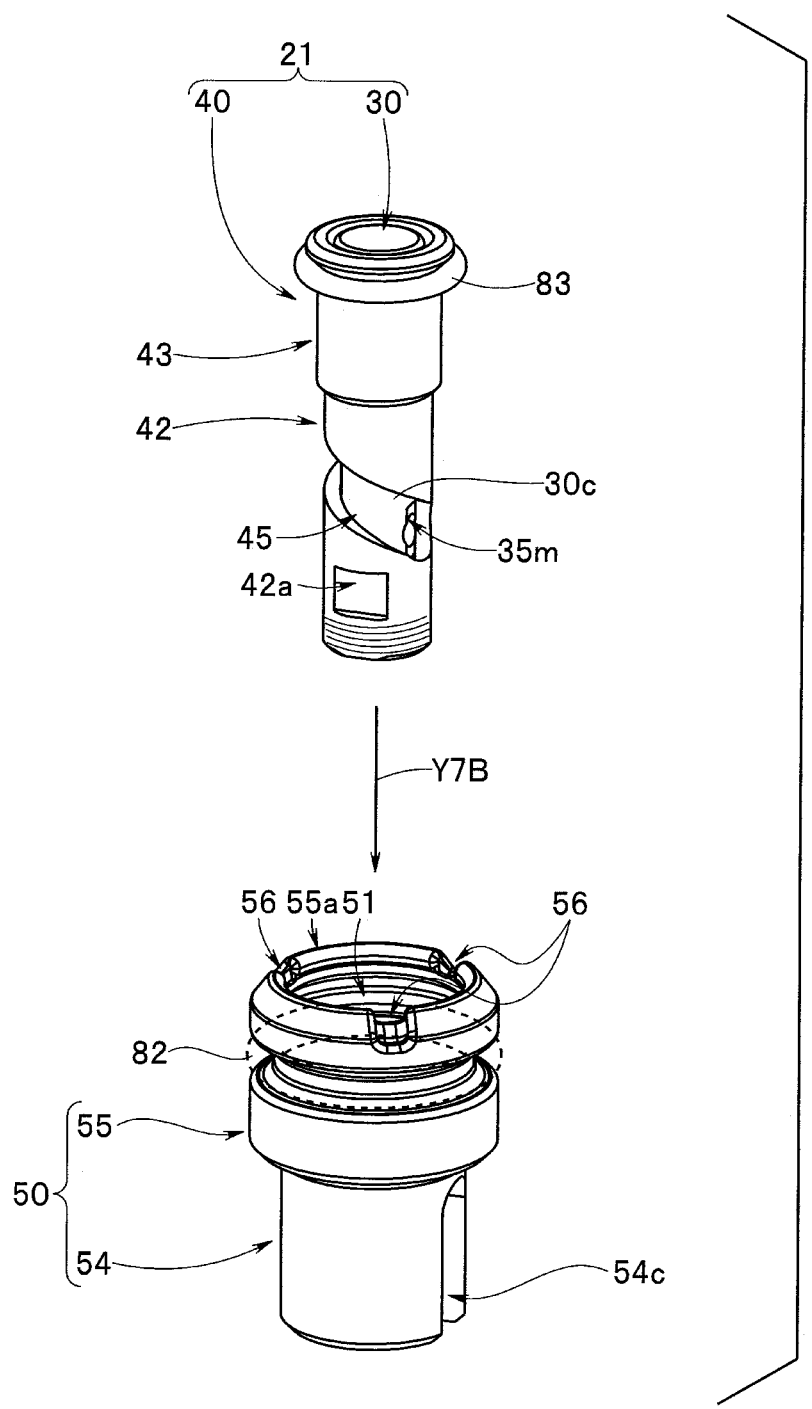
FIG. 7B is a view explaining a relationship between a first integrated set and the rotational member.

Next, the operator inserts the shaft body 30 into the shaft body hole 41 of the tubular member 40 as illustrated by an arrow Y7A, and disposes the shaft body 30 in the shaft body hole 41. As a result, a first integrated set 21 is formed as illustrated in FIG. 7B. The first integrated set 21 is such that the two members that are the shaft body 30 and the tubular member 40 are integrated.

Note that in the first integrated set 21, the thread opening 35m of the shaft body 30 has a position adjusted so as to be exposed through a vicinity of a lowest point of the cam groove 45 of the tubular member 40.

Next, the operator inserts the first integrated set 21 into the tubular member hole 51 of the rotational member 50 as shown by an arrow Y7B in FIG. 7B.

At this time, the operator disposes the third O-shaped ring 83 in the inner circumferential groove 53i while adjusting a position so that the thread opening 35m is exposed through the cam pin groove 54c. Thereafter, the thin pin portion 71 of the cam pin 70 is screwed into the pin fixing portion 35.

Figure 7C:
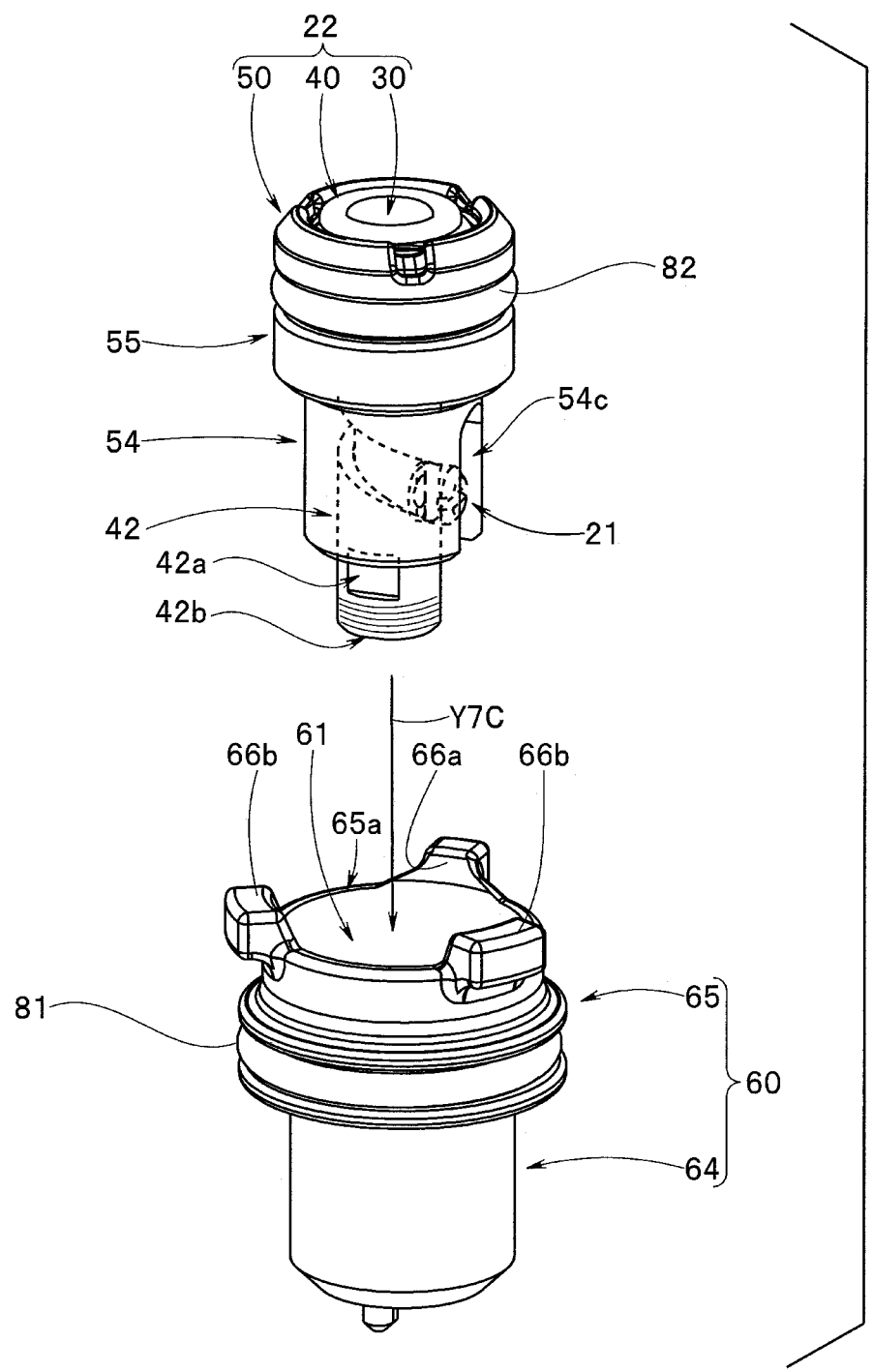
FIG. 7C is a view explaining a relationship between a second integrated set and the housing member.

As a result, as illustrated in FIG. 7C, the cam pin 70 is integrally provided in the shaft body 30, and a second integrated set 22 is formed. The second integrated set 22 is such that the three members that are the shaft body 30, the tubular member 40, and the rotational member 50 are integrated. Note that the thick pin portion 72 is disposed in the cam pin groove 54c.

Next, the operator inserts the second integrated set 22 into the housing hole 61 of the housing member 60 as shown by an arrow Y7C in FIG. 7C. In FIG. 7C, the first O-shaped ring 81 is fitted in the outer circumferential groove 65o of the adaptor attaching portion 65 in advance.

At this time, the cam forming portion 42 is inserted into the tubular member positioning hole 60h after the defining surface 42a of the cam forming portion 42 protruding from the cam support portion end surface 54a of the rotational member 50 and the straight portion 60s of the tubular member positioning hole 60h are faced to each other.

Figure 7D:
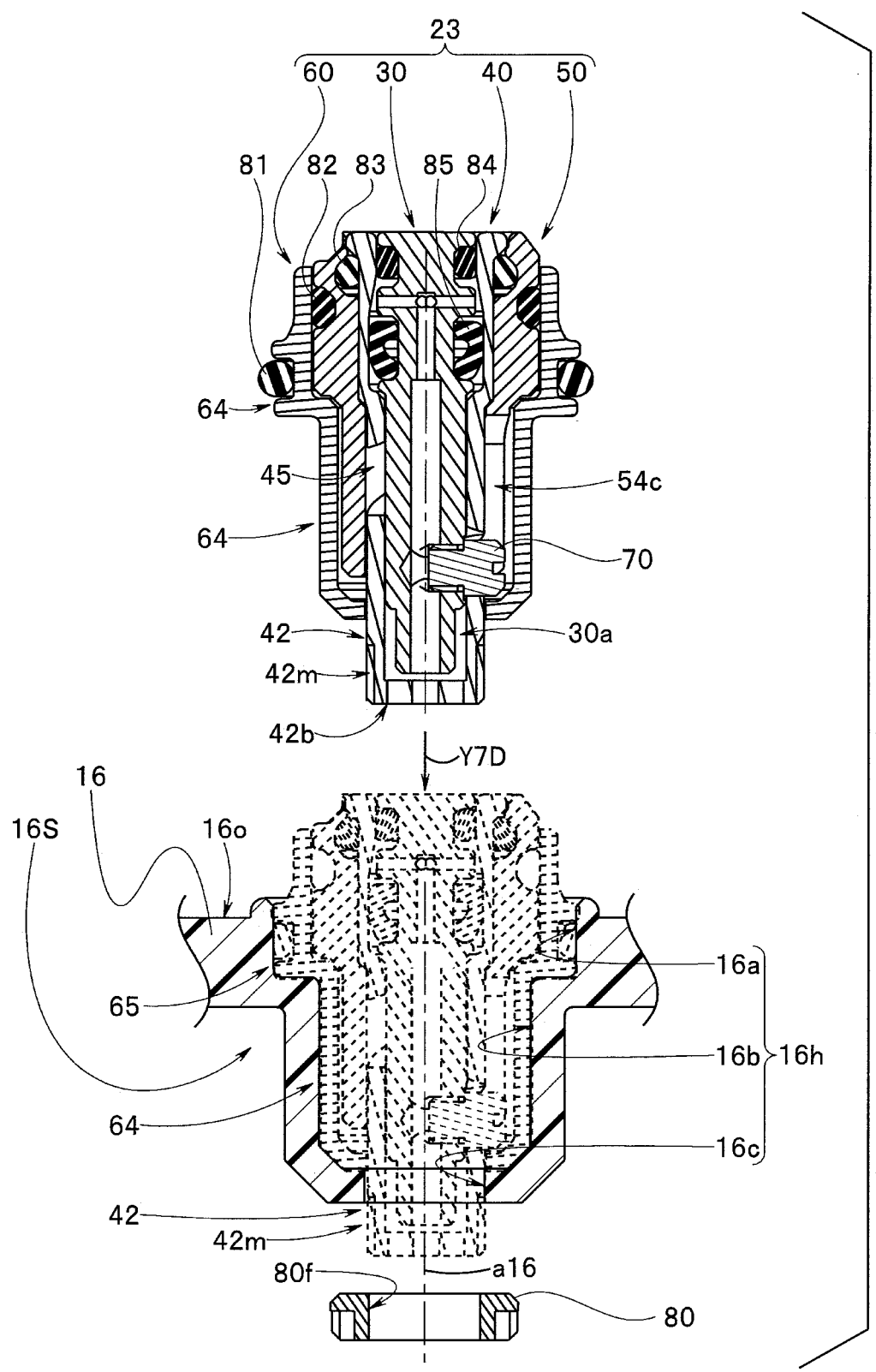
FIG. 7D is a view explaining attachment of a third integrated set to a pipe sleeve hole.

As a result, a third integrated set 23 as illustrated in FIG. 7D is formed. The third integrated set 23 is such that the four members that are the shaft body 30, the tubular member 40, the rotational member 50, and the housing member 60 are integrated.

Here, attachment of the third integrated set 23 to the pipe sleeve hole 16h is described.

The operator disposes the third integrated set 23 in the pipe sleeve hole 16h of the endoscope connector 16 as shown by an arrow Y7D in FIG. 7D.

The pipe sleeve hole 16h is a stepped hole, and includes a watertightness maintaining hole 16a, a rotational hole 16b, and a connection hole 16c in order from an outer surface 16o side.

The operator inserts the third integrated set 23 into the watertightness maintaining hole 16a, the rotational hole 16b, and the connection hole 16c in this order at the time of assembly. As a result, the cam forming portion 42 protruded from the connector attaching portion 64 is disposed to protrude from the connection hole 16c as shown by a broken line, the connector attaching portion 64 is disposed in the rotational hole 16b, and a predetermined site of the adaptor attaching portion 65 where the first O-shaped ring 81 is placed is disposed in the watertightness maintaining hole 16a.

Next, the operator screws a female thread 80f of the fixing nut 80 onto the male thread portion 42m of the cam forming portion 42. Thereupon, the tubular member 40 presses the rotational member 50 while the tubular member 40 is fastened, and the rotational member 50 further presses the housing member 60 into the pipe sleeve hole 16h.

As a result, the third integrated set 23 is fixedly provided in the pipe sleeve hole 16h, and the endoscope connector 16 where the vent pipe sleeve 20 is disposed as illustrated in FIG. 2 described above is obtained.

In the vent pipe sleeve 20 provided in the endoscope connector 16 in this way, the first O-shaped ring 81 maintains watertightness between the inner peripheral surface of the watertightness maintaining hole 16a of the pipe sleeve hole 16h, and the outer peripheral surface of the adaptor attaching portion 65 of the housing member 60. The second O-shaped ring 82 maintains watertightness between the inner peripheral surface of the main body housing hole 63 of the housing member 60 and the outer circumferential surface of the rotational main body 55 of the rotational member 50. In addition, the third O-shaped ring 83 maintains watertightness between the inner peripheral surface of the main body portion hole 53 of the rotational member 50 and the outer peripheral surface of the main body portion 43 of the tubular member 40. The fourth O-shaped ring 84 maintains watertightness between the inner peripheral surface of the watertightness maintaining portion 41a of the tubular member 40 and the outer peripheral surface of the large diameter portion 30b of the shaft body 30. Accordingly, the inside of the connector space 16S of the endoscope connector 16 is kept watertight with respect to the outside.

In the vent pipe sleeve 20 provided in the endoscope connector 16, the three engaging holes 56 are provided as described above. Disposing positions of these engaging holes 56 are set as illustrated in FIG. 7E.

Figure 7E:
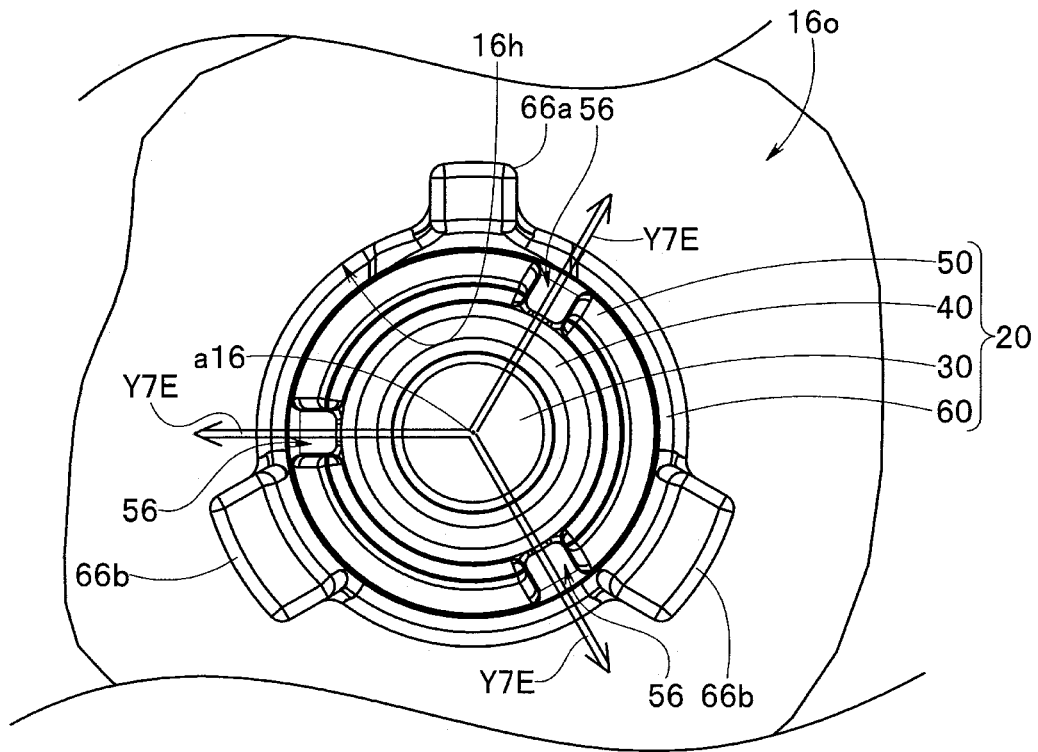
FIG. 7E is a view of the vent pipe sleeve of the endoscope connector seen in an arrow Y7E direction in FIG. 2.

More specifically, the placement position of the engaging hole 56 is set so that brushing can be performed without movement of a brush being hindered by the protruding portions 66a and 66b, when a hole bottom surface of the engaging hole 56 is brushed outward of the pipe sleeve 20 from a hole center axis a16 side as shown by an arrow Y7E in FIG. 7E, or brushed toward the hole center axis a16 oppositely to the arrow.

Thereby, the hole bottom surface of the engaging hole 56 can be brushed reliably and easily when the outer surface of the endoscope connector 16 is brushed.

Figure 8A:
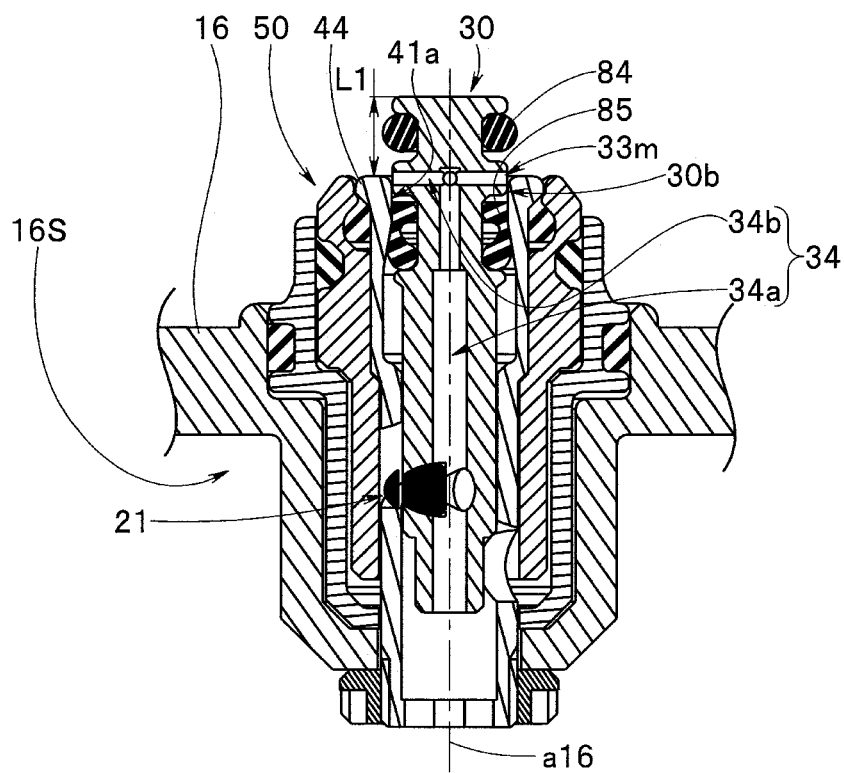
FIG. 8A is a view explaining a state where the shaft body is protruded by L1 from an outer end surface of an outer flange.
Figure 8B:
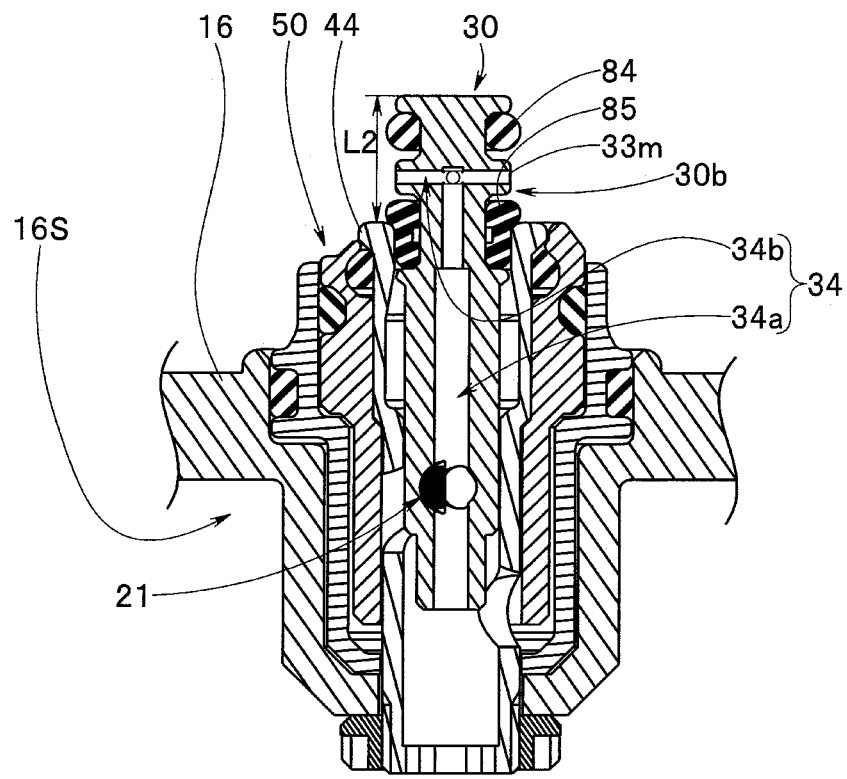
FIG. 8B is a view explaining a state where the shaft body is protruded by L2 from the outer end surface of the outer flange.

In the vent pipe sleeve 20, the shaft body 30 moves along the hole center axis a16. It is possible to perform vent control by causing the outer end surface of the large diameter portion 30b of the shaft body 30 to protrude from the outer end surface of the outer flange 44 of the tubular member 40 as illustrated in FIG. 8A and FIG. 8B, for example.

In the present embodiment, the shaft body 30 moves along the hole center axis a16 by causing engaging claws of a jig (not illustrated) to engage with the three engaging holes 56 provided in the rotational member 50, and causing the rotational member 50 to rotate in a clockwise direction, or a counterclockwise direction by the jig.

Note that the shaft body 30 is movable only outward along the hole center axis a16 when the vent pipe sleeve 20 illustrated in FIG. 2 keeps the inside of the connector space 16S watertight.

More specifically, by causing the rotational member 50 of the vent pipe sleeve 20 illustrated in FIG. 2 to rotate by the jig, the thick pin portion 72 of the cam pin 70 is moved along the cam pin groove 54c while sliding in the cam groove 45.

The thin pin portion 71 of the cam pin 70 is fixedly provided in the shaft body 30. Accordingly, the shaft body 30 moves outward along the hole center axis a16 with rotation of the rotational member 50. When the rotational member 50 is caused to rotate a predetermined angle in the present embodiment, the outer end surface of the large diameter portion 30b of the shaft body 30 is disposed L1 away from the outer end surface of the outer flange 44 of the tubular member 40 as illustrated in FIG. 8A.

At this time, the fourth O-shaped ring 84 is disposed in the outside, and the vent opening 33m of the shaft body 30 is exposed to the outside. As a result, the outside and the inside of the connector space 16S are brought into a communicating state by the vent hole 34.

At this time, the fifth O-shaped ring 85 is disposed in a first position to closely contact the watertightness maintaining portion 41a to maintain watertightness between the tubular member 40 and the shaft body 30.

Note that when the rotational member 50 is further caused to rotate a predetermined angle in the present embodiment, the outer end surface of the large diameter portion 30b is disposed L2 away from the outer end surface of the outer flange 44 of the tubular member 40 as illustrated in FIG. 8B.

At this time, a part of the fifth O-shaped ring 85 is in a state of protruding from the outer end surface of the outer flange 44 to the outside, and a remaining part closely contacts the watertightness maintaining portion 41a to maintain watertightness between the tubular member 40 and the shaft body 30.

Figure 9:
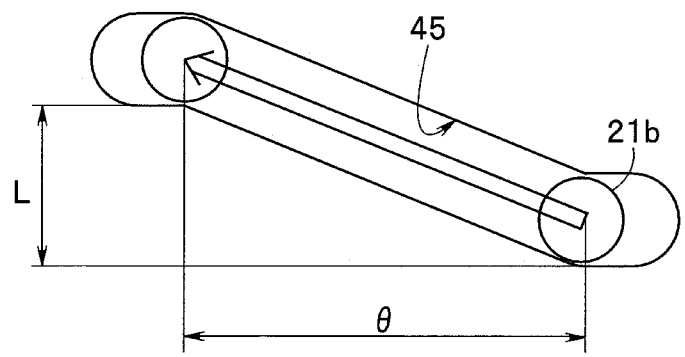
FIG. 9 is a cam diagram of a cam groove where a thick pin portion of a cam pin slides.

Note that the cam groove 45 is set so that the thick pin portion 72 moves a predetermined distance (L) by the rotational member 50 being caused to rotate an angle (θ) as illustrated in a cam diagram in FIG. 9.

More specifically, when the rotational member 50 is caused to rotate 270 degrees that is a first angle from an initial position (0 degrees) in the present embodiment, the shaft body 30 moves in the axial direction. In other words, the shaft body 30 moves from a first position illustrated in FIG. 12A described later where the fourth O-shaped ring 84 closely contacts the watertightness maintaining portion 41a to a second position illustrated in FIG. 15A described later where the fifth O-shaped ring 85 closely contacts the watertightness maintaining portion 41a and a fifth ring housing portion 122, and the fourth O-shaped ring 84 closely contacts a fourth ring housing portion 121.

In the cam groove 45, a relief is provided as illustrated in the cam diagram, so that the first position and the second position are stably kept.

Note that the first angle is not limited to 270 degrees, and is set within a range of less than one rotation.

In this way, the vent pipe sleeve 20 of the endoscope connector 16 of the present embodiment maintains the inside of the connector space 16S watertight with respect to the outside by the fourth O-shaped ring 84 closely contacting the inner peripheral surface of the watertightness maintaining portion 41a in addition to the first O-shaped ring 81, the second O-shaped ring 82, and the third O-shaped ring 83. The fourth O-shaped ring 84 is one of the O-shaped rings provided at the shaft body 30.

Accordingly, it is possible to reliably prevent a cleaning solution from entering the connector space 16S while cleaning a vicinity of the vent pipe sleeve 20.

The shaft body 30 moves by the cam pin 70 sliding along the cam groove 45. Accordingly, the cam pin 70 is not caused to slide along the cam groove 45 by pressing the outer end surface of the large diameter portion 30b of the shaft body 30 exposed to the outside of the vent pipe sleeve 20 in a connector space 16S direction.

Consequently, even when the operator erroneously presses the outer end surface of the shaft body 30 during cleaning or the like, it is possible to reliably maintain watertightness.

The endoscope 2 of the present embodiment is subjected to autoclave sterilization after being cleaned.

At a time of autoclave sterilization, an adaptor 10 having a function of the aforementioned jig is fitted to the vent pipe sleeve 20. The adaptor 10 has a check valve unit 100 and a pipe sleeve control unit 110 illustrated in FIG. 10, for example.

The check valve unit 100 includes a cylindrical exterior body 101, a rod-shaped valve shaft 102, a spring 103 that is an urging member, a falling prevention plate 104, a check valve O-shaped ring 105, and a watertightness O-shaped ring 106.

The falling prevention plate 104 is fixedly provided at an end surface of the valve shaft 102 to prevent the spring 103 from falling off from the valve shaft 102. The check valve O-shaped ring 105 closely contacts a slanting surface 108 of a shaft hole 107 by an elastic force of the spring 103.

Reference sign 111 denotes a connection cylinder 111 of the pipe sleeve control unit 110. The exterior body 101 is attachable to and detachable from the connection cylinder 111. When the exterior body 101 is fitted on the connection cylinder 111, watertightness between an inner peripheral surface of the exterior body 101 and an outer peripheral surface of the connection cylinder 111 is maintained by the watertightness O-shaped ring 106.

Note that it is possible to attach a water leakage checker to the connection cylinder 111 in place of the check valve unit 100.

The pipe sleeve control unit 110 will be described with reference to FIG. 10, FIG. 11A, FIG. 11B, and FIG. 11C.

Figure 10:
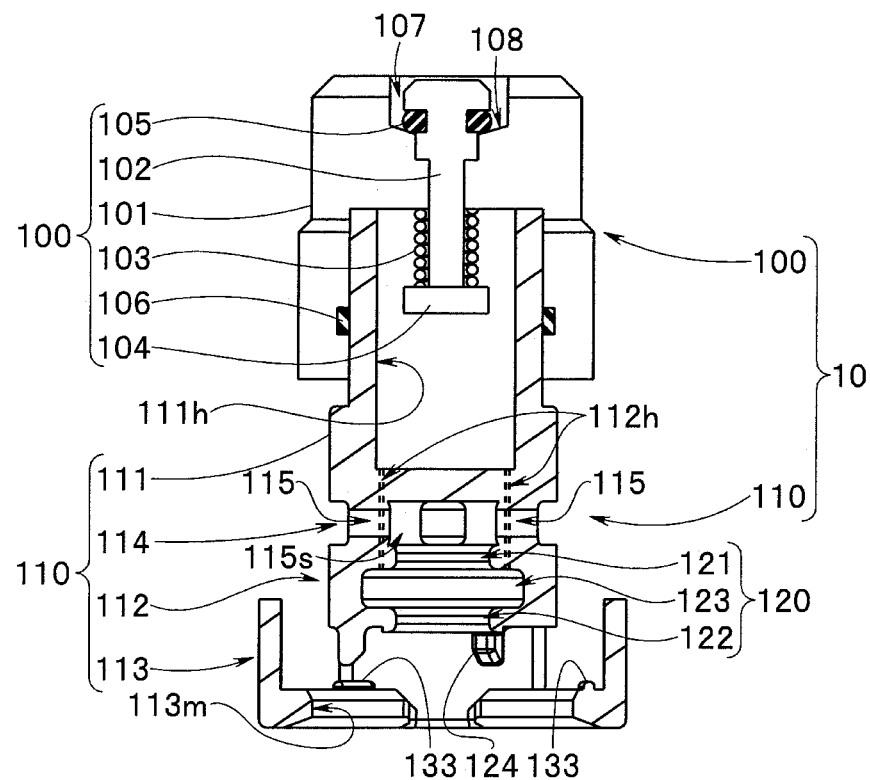
FIG. 10 is a view explaining an adaptor having a check valve unit and a pipe sleeve control unit.
Figure 11A:
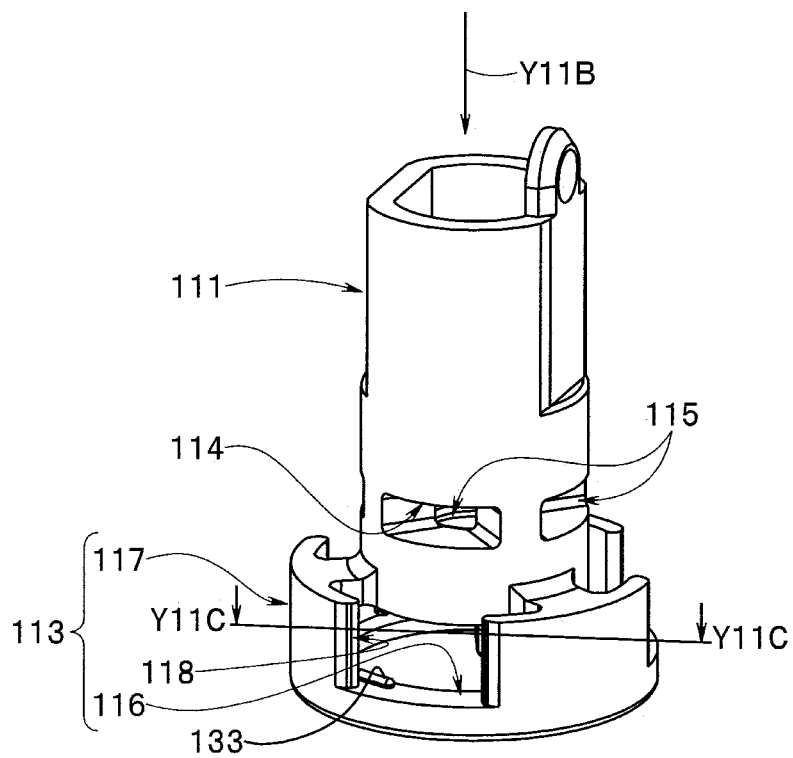
FIG. 11A is a perspective view explaining the pipe sleeve control unit.

As illustrated in FIG. 10 and FIG. 11A, the pipe sleeve control unit 110 includes the connection cylinder 111, a unit main body 112, and a receiving portion 113. Reference sign 114 denotes a vent port, which is provided between the connection cylinder 111 and the unit main body 112. The vent port 114 is an opening of a flow path 115. The vent port 114 communicates with a housing space 120 via a communication space 115s.

Figure 11B:
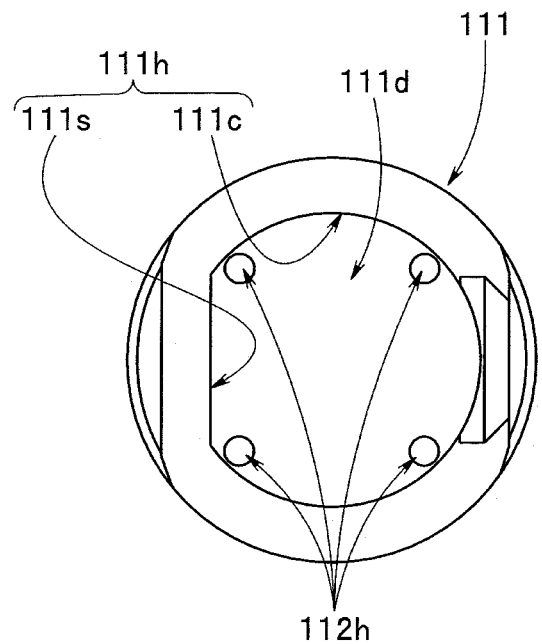
FIG. 11B is a view explaining a connection cylinder of the pipe sleeve control unit, and is a view of the connection cylinder seen in a Y11B direction in FIG. 11A.

As illustrated in FIG. 11B, a cylinder hole 111h is in a D-shape where a curved surface 111c and a straight surface 111s are disposed. As illustrated in FIG. 10 and FIG. 11B, the housing space 120 and an inside of the cylinder hole 111h communicate with each other by a plurality of open holes 112h. The open holes 112h include, for example, four openings in a cylinder bottom surface 111d of the cylinder hole 111h. A number of open holes 112h is preferably four, but may be more than four or may be less than four.

Note that the housing space 120 is a space in which the large diameter portion 30b of the shaft body 30 is housed. The housing space 120 is provided in a central portion of the unit main body 112. The housing space 120 has a fourth ring housing portion 121, a fifth ring housing portion 122, and a boundary surface housing portion 123, An inside diameter of the boundary surface housing portion 123 is set to be larger than an inside diameter of the fourth ring housing portion 121 and an inside diameter of the fifth ring housing portion 122.

The fourth O-shaped ring 84 passing through the fifth ring housing portion 122, and the boundary surface housing portion 123 is disposed in close contact with an inner peripheral surface of the fourth ring housing portion 121. The fifth O-shaped ring 85 is disposed in close contact with an inner peripheral surface of the fifth ring housing portion 122. The boundary surface 33 having the vent openings 33m passing through the fifth ring housing portion 122 is disposed in the boundary surface housing portion 123.

Reference sign 124 denotes a locking portion. The locking portion 124 is a protrusion configured to engage with the engaging hole 56. In the present embodiment, three locking portions 124 that are respectively engaged with the aforementioned three engaging holes 56 are provided to protrude from a support portion side end surface of the unit main body 112.

Figure 11C:
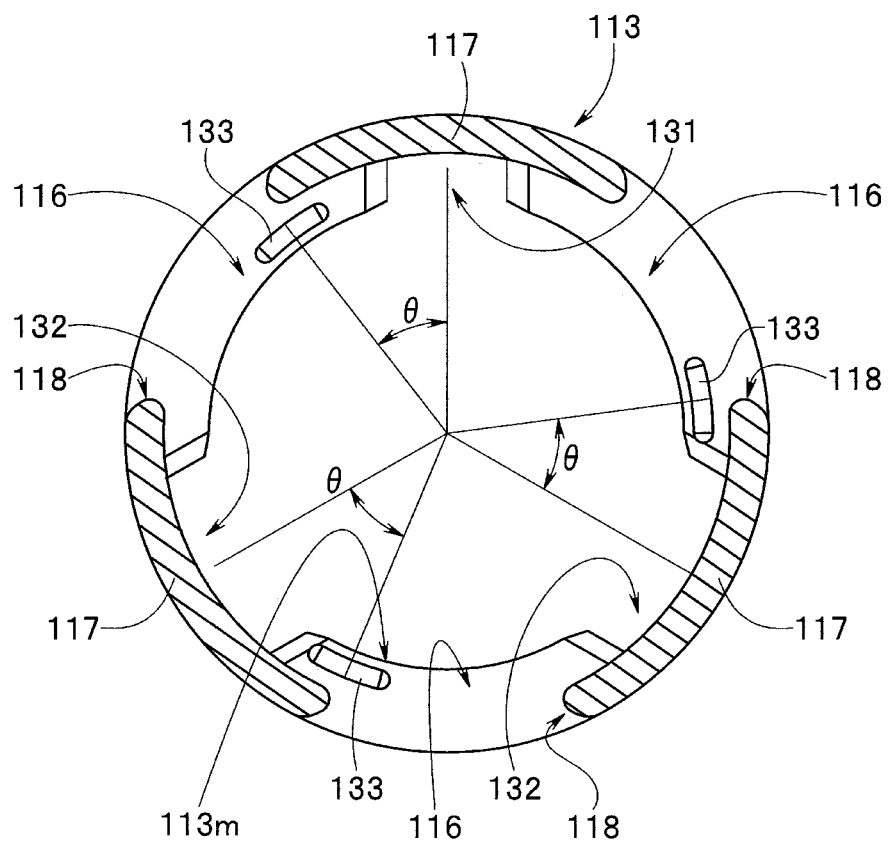
FIG. 11C is a sectional view along a line Y11C in FIG. 11A explaining a receiving portion of the pipe sleeve control unit.

As illustrated in FIG. 10 to FIG. 11C, the receiving portion 113 is in a cylindrical shape. The receiving portion 113 has a ring-shaped plate portion 116, and a plurality of wall portions 117. The wall portions 117 are vertically provided from one flat surface of the plate portion 116 forming a bottom surface of the receiving portion 113. The vertically provided wall portions 117 are divided by cutouts 118. The cutout 118 is a so-called vent passage causing the inside of the receiving portion 113 and the outside to communicate with each other. Reference sign 113m denotes a receiving portion opening.

In the plate portion 116, a first protrusion recessed portion (hereinafter, described as a first relief groove) 131, two second protrusion recessed portions (hereinafter, described as second relief grooves) 132, and a protruding portion receiver 133 are disposed.

The first relief groove 131 is set to have such a width that the first protruding portion 66a can pass through. The second relief groove 132 is set to have such a width that the second protruding portion 66b can pass through.

The protruding portion receiver 133 is a protruded portion with a semicircular sectional shape protruding with a predetermined height from the one flat surface of the plate portion 116. Three protruding portion receivers 133 are disposed on the one flat surface of the plate portion 116 at substantially equal intervals in a circumferential direction. Central portions of the protruding portion receivers 133 are displaced by a predetermined angle θ with respect to a central portion of the first relief groove 131 and central portions of the second relief grooves 132.

A length in a circumferential direction of the protruding portion receiver 133 is set to a predetermined length in consideration of widths w1 and w2 of the protruding portions 66a and 66b. End portions in the circumferential direction of the protruding portion receiver 133 are formed by curved surfaces, or smooth slanting surfaces.

A width of the first relief groove 131 is set so that the second protruding portion 66b cannot pass through. Accordingly, it is impossible to fit the pipe sleeve control unit 110 to the vent pipe sleeve 20 in a state where the second protruding portion 66b is faced to the first relief groove 131. In other words, when the rotation angle after fitting changes from 0 degrees to 120 degrees and the relief groove and the protruding portion correspond to each other, and when the rotation angle further changes by 120 degrees to change to 240 degrees and the relief groove and the protruding portion correspond to each other, during a fitting operation, the second protruding portion 66b cannot pass the first relief groove 131. In other words, the pipe sleeve control unit 110 is reliably prevented from falling off from the vent pipe sleeve 20 during fitting.

Here, with reference to FIG. 12A to FIG. 15B, fitting of the adaptor 10 to the vent pipe sleeve 20 will be described.

When performing autoclave sterilization, the operator firstly causes the first relief groove 131 of the receiving portion opening 113m of the pipe sleeve control unit 110 disposed in the adaptor 10 to face the first protruding portion 66a of the vent pipe sleeve 20 protruded from the endoscope connector 16. The operator brings the three locking portions 124 close to the engaging holes 56 while guiding the first protruding portion 66a into the first relief groove 131. As a result, the pipe sleeve control unit 110 is disposed in the vent pipe sleeve 20 as illustrated in FIG. 12A and FIG. 12B.

At this time, the first protruding portion 66a is introduced into the first relief groove 131, and the two second protruding portions 66b are respectively introduced into the second relief grooves 132. The three locking portions 124 respectively engage with the engaging holes 56. The straight surface 111s of the cylinder hole 111h is located as shown by a broken line in FIG. 14.

Figure 12A:
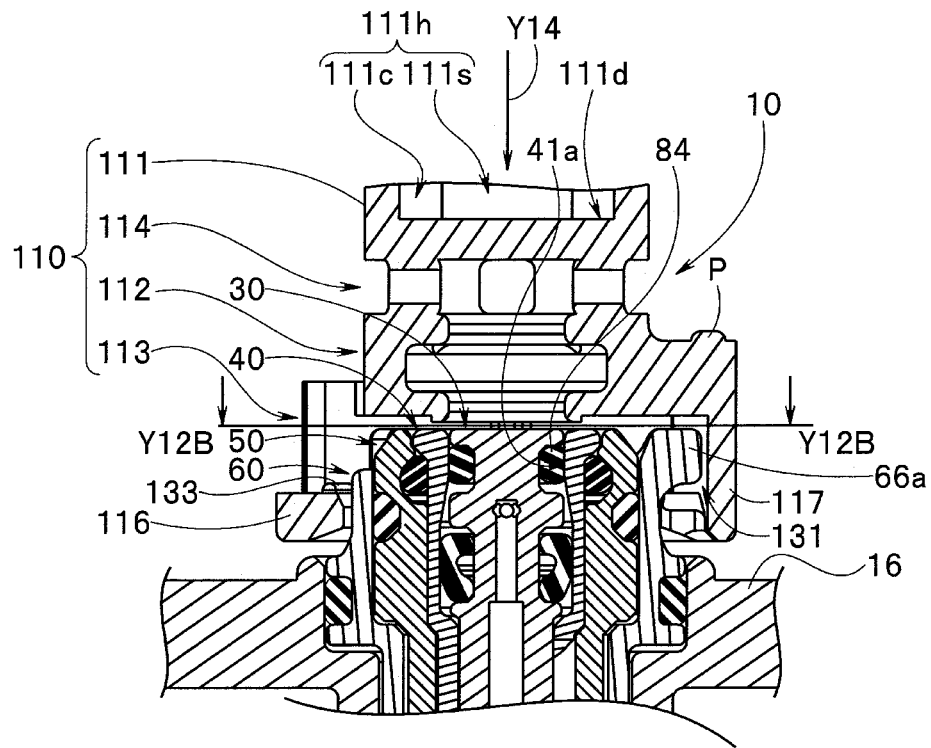
FIG. 12A is a view illustrating the vent pipe sleeve and the pipe sleeve control unit disposed on the vent pipe sleeve.
Figure 12B:
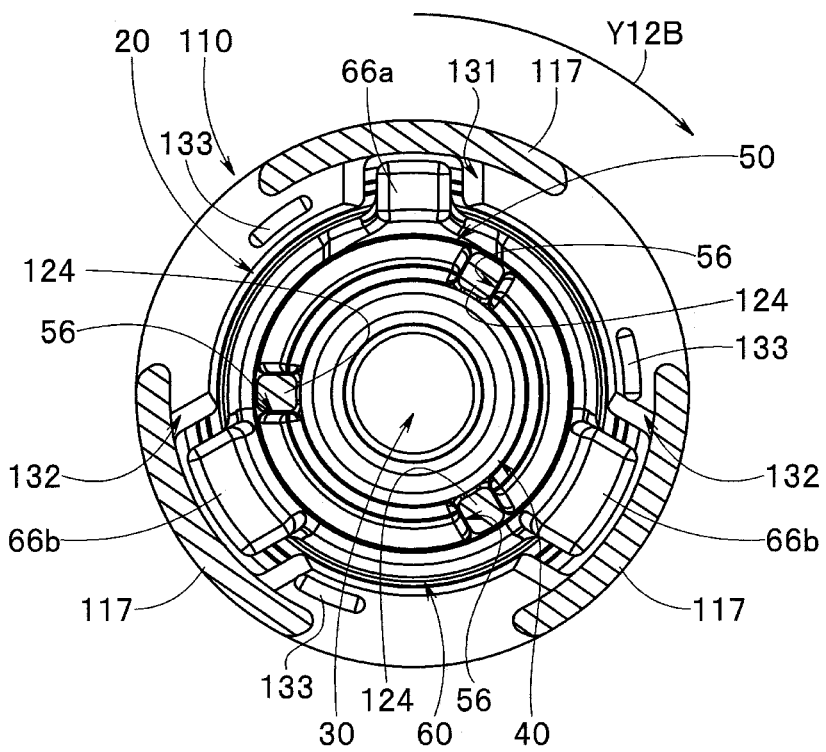
FIG. 12B is a sectional view taken along a line of arrows Y12B to Y12B in FIG. 12A.

Next, the operator causes the pipe sleeve control unit 110 to rotate in a direction shown by an arrow Y12B in FIG. 12B to start a fitting operation. Since the locking portions 124 are disposed in the engaging holes 56, the rotational member 50 is rotated with rotation of the pipe sleeve control unit 110, and the relief grooves 131 and 132, and the protruding portion receiver 133 move.

Note that reference sign P in FIG. 12A denotes a semispherical protruded portion. The semispherical protruded portion P is visually recognizable by the operator, and is a marker for visually recognizing a rotation angle at a time of causing the pipe sleeve control unit 110 to rotate.

Figure 13A:
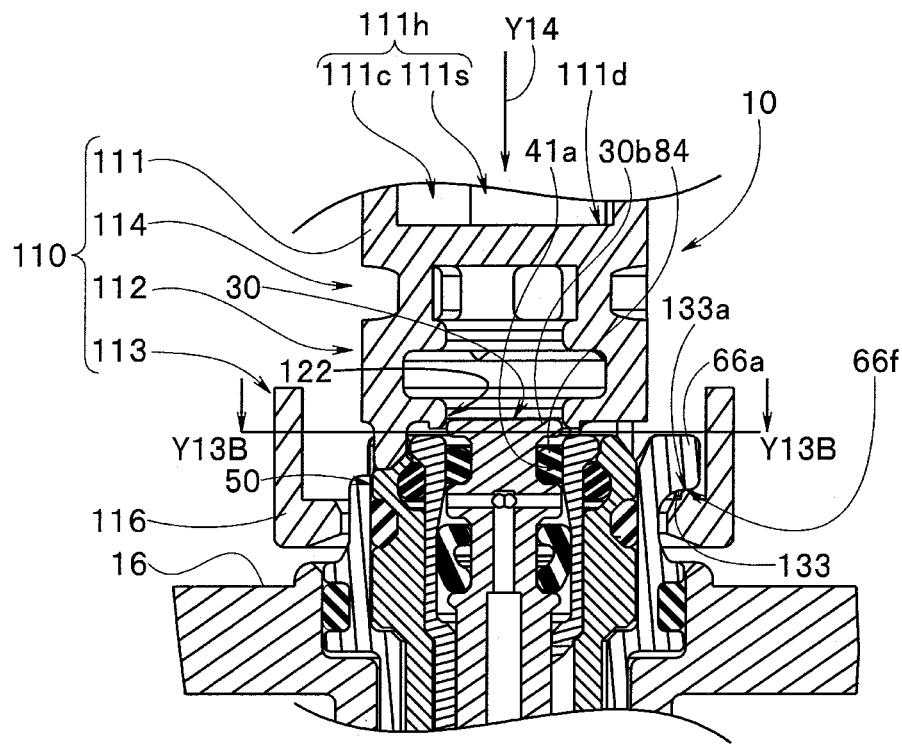
FIG. 13A is a view at a time of the pipe sleeve control unit disposed on the vent pipe sleeve being rotated 30 degrees.
Figure 13B:
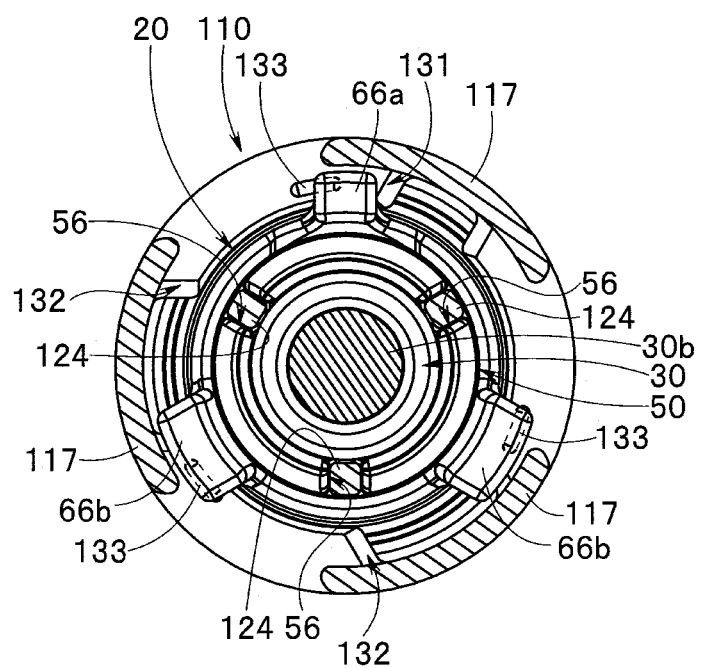
FIG. 13B is a sectional view taken along a line of arrows Y13B to Y13B in FIG. 13A.
Figure 14:
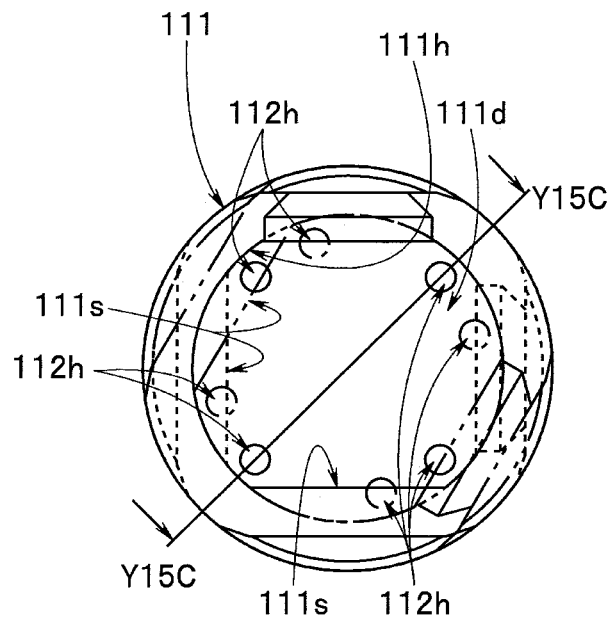
FIG. 14 is a view of an inside of a cylinder hole in FIG. 12A, an inside of a cylinder hole in FIG. 13A, and an inside of a cylinder hole in FIG. 15A seen in an arrow Y14 direction.

The operator causes the pipe sleeve control unit 110 to rotate, for example, 30 degrees. Then, curved surface top portions 133a of the protruding portion receivers 133 respectively provided in vicinities of the relief grooves 131 and 132 are disposed to abut on inclined receiving surfaces 66f of the protruding portions 66a and 66b as illustrated in FIG. 13A and FIG. 13B. At this time, as illustrated in FIG. 14, the straight surface 111s of the cylinder hole 111h also rotates 30 degrees and is moved as shown by a two-dot chain line.

As a result, the protruding portions 66a and 66b are supported substantially by three points at the curved surface top portions 133a at three spots, and are in a state of separating (floating) with respect to one flat surface of the plate portion 116, except for contact portions of the inclined receiving surfaces 66f.

The outer end surface of the large diameter portion 30b of the shaft body 30 is protruded outward from the outer end surface of the tubular member 40 with rotation of 30 degrees of the rotational member 50. Then, a part at an outer end surface side of the large diameter portion 30b enters the fifth ring housing portion 122.

The operator further causes the pipe sleeve control unit 110 to rotate 240 degrees. At this time, the straight surface 111s of the cylinder hole 111h rotates 270 degrees from an initial position shown by a broken line to be disposed as shown by a solid line as illustrated in FIG. 14.

Figure 15A:
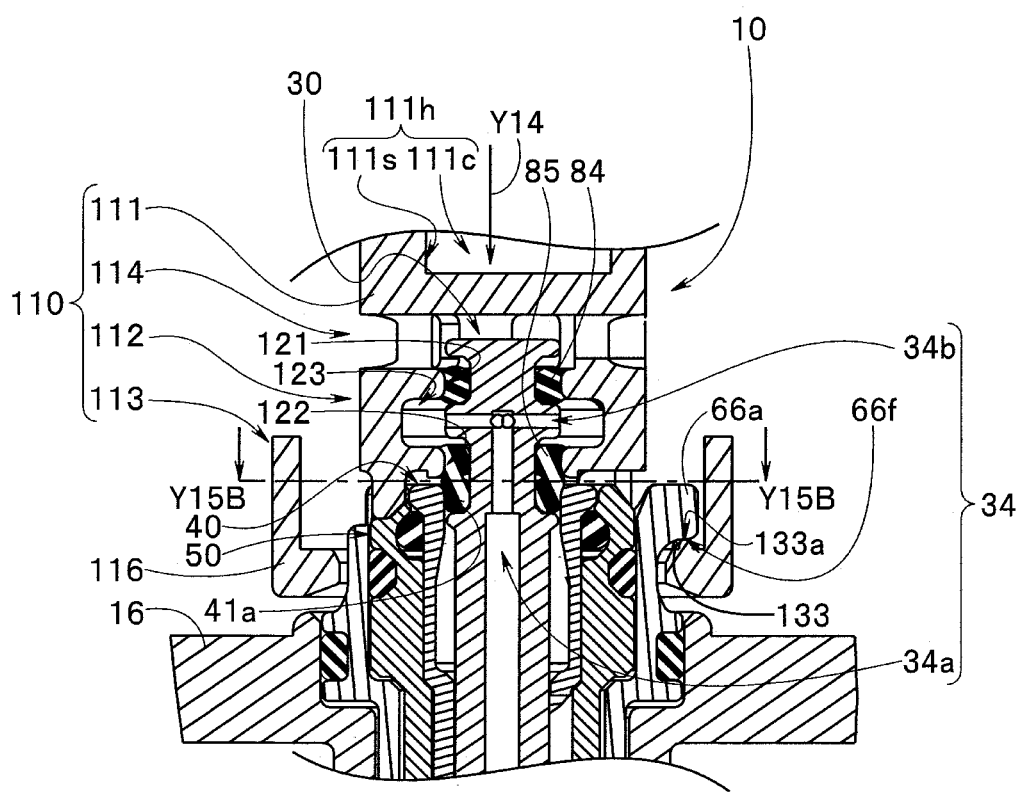
FIG. 15A is a view of the pipe sleeve control unit being fitted to the vent pipe sleeve.
Figure 15B:
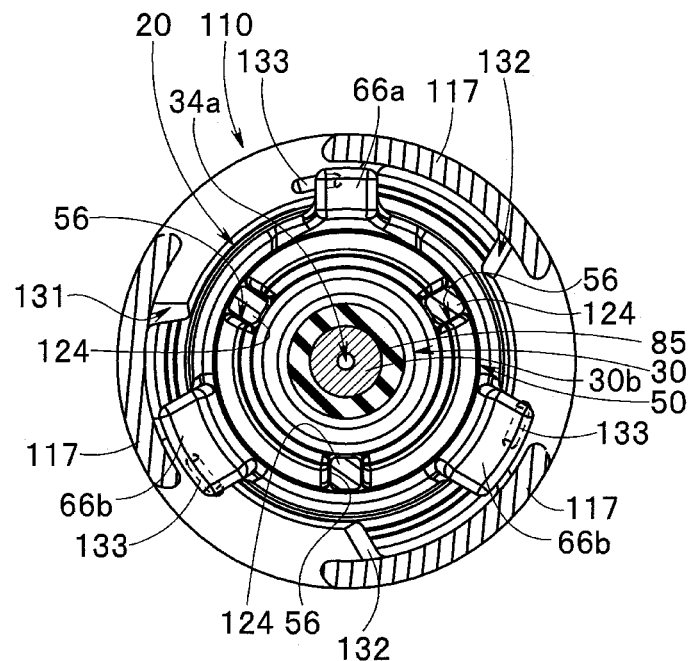
FIG. 15B is a sectional view taken along a line of arrows Y15B to Y15B in FIG. 15A.

As a result, the pipe sleeve control unit 110 is caused to rotate 270 degrees to be in a fitted state to the vent pipe sleeve 20 as illustrated in FIG. 15A and FIG. 15B.

At this time, as illustrated in FIG. 15A, the fourth O-shaped ring 84 provided at the large diameter portion 30b of the shaft body 30 closely contacts the inner peripheral surface of the fourth ring housing portion 121. A part of the fifth O-shaped ring 85 protrudes to the outside from the outer end surface of the outer flange 44 and closely contacts the inner peripheral surface of the fifth ring housing portion 122.

In addition, the other part than the aforementioned one part of the fifth O-shaped ring 85 is in close contact with the inner peripheral surface of the watertightness maintaining portion 41a of the tubular member 40.

Figure 15C:
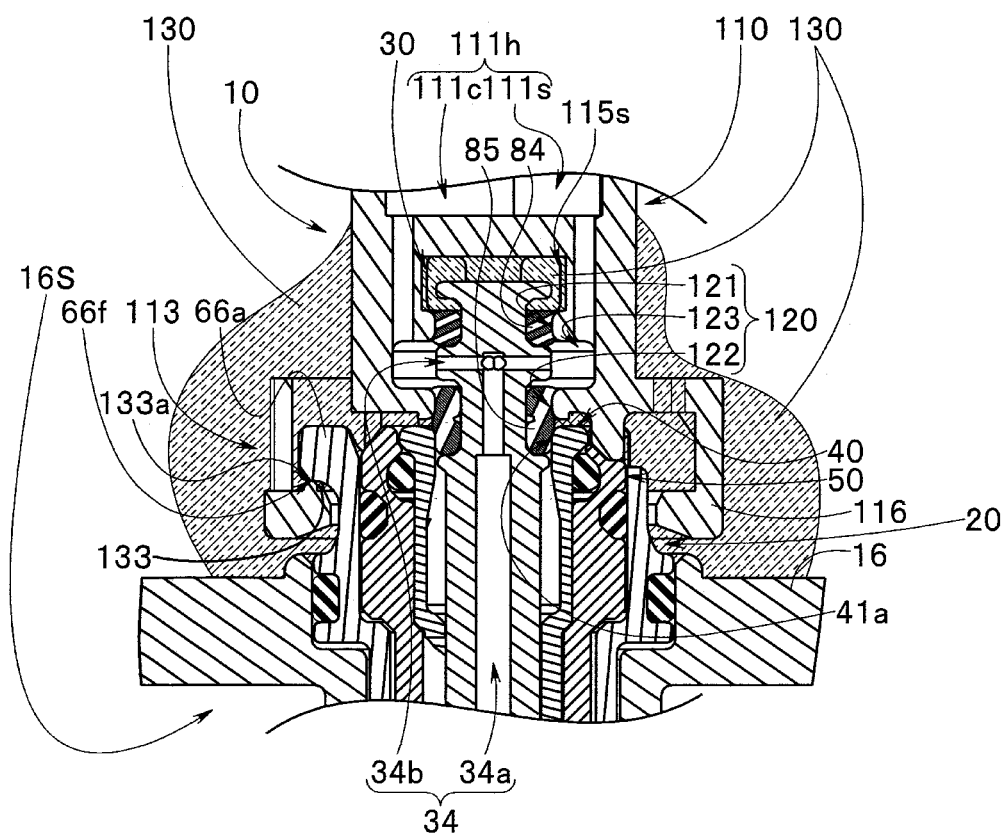
FIG. 15C is a sectional view taken along a line of arrows Y15C to Y15C in FIG. 14, and is a view explaining a state where the vent pipe sleeve to which the adaptor is fitted is exposed to sterilizing steam.

At this time, as illustrated in FIG. 15C, the cylinder hole 111h and the connector space 16S are in a state of communicating with each other by the open holes 112h, and the vent hole 34 opening to the boundary surface housing portion 123 where the aforementioned boundary surface 33 is disposed.

At this time, the check valve O-shaped ring 105 is in close contact with the slanting surface 108 of the shaft hole 107 by the urging force of the spring 103. Accordingly, when the pipe sleeve control unit 110 is in a state of being fitted to the vent pipe sleeve 20, the inside of the connector space 16S and the outside are kept watertight.

In this way, the check valve unit 100 is provided in the pipe sleeve control unit 110 provided with the locking portions 124 that engage with the engaging holes 56 provided in the rotational member 50 to form the adaptor 10. The locking portions 124 are caused to engage with the engaging holes 56, and the pipe sleeve control unit 110 is rotated 270 degrees in this state.

Thereby, it is possible to fit the adaptor 10 to the vent pipe sleeve 20. At this time, the inside of the connector space 16S is kept watertight with respect to the outside.

As described above, the endoscope 2 with the adaptor 10 fitted to the vent pipe sleeve 20 is left in the chamber and is exposed to sterilizing steam at a time of autoclave sterilization.

At this time, as illustrated in FIG. 15C, sterilizing steam 130 enters the communication space 115s from a periphery of the adaptor 10 and a periphery of the endoscope connector 16, and the flow path 115 and sterilizes the periphery of the adaptor 10, the periphery of the endoscope connector 16, the outer end surface of the large diameter portion 30b, and a periphery of the outer end surface.

The sterilizing steam 130 enters the receiving portion 113, and sterilizes surfaces exposed to the outside, of the protruding portions 66a and 66b, in addition to the outer end surface exposed to the outside, of the tubular member 40 and a periphery of the outer end surface, the outer end surface exposed to the outside, of the rotational member 50 and a periphery of the outer end surface, and the outer end surface exposed to the outside, of the housing member 60 and a periphery of the outer end surface. The sterilizing steam 130 further sterilizes the inclined receiving surface 66f supported by the curved surface top portion 133a, and a gap of the inclined receiving surface 66f.

In other words, it is possible to obtain an endoscope to which reliable sterilization is applied by reliably distributing the sterilizing steam 130 to the exposed surfaces during the procedure.

Note that when a pressure in the connector space 16S becomes higher than a pressure of the outside, the valve shaft 102 is moved against the urging force of the spring 103 and close contact of the check valve O-shaped ring 105 to the slanting surface 108 is released, and the inside of the connector space 16S and the outside communicate with each other by the vent hole 34, the open holes 112h, and the cylinder hole 111h.

In the present embodiment, the sterilizing steam 130 cannot enter the boundary surface housing portion 123. In other words, the boundary surface 33 of the shaft body 30 and a periphery of the boundary surface 33 are not sterilized.

However, the boundary surface 33 and the periphery of the boundary surface 33 cannot be parts exposed to the outside, in the vent pipe sleeve 20 that keeps the inside of the connector space 16S illustrated in FIG. 2 watertight with respect to the outside. In other words, the boundary surface 33 and the periphery of the boundary surface 33 are regions that do not require sterilization by the sterilizing steam.

Figure 16A:
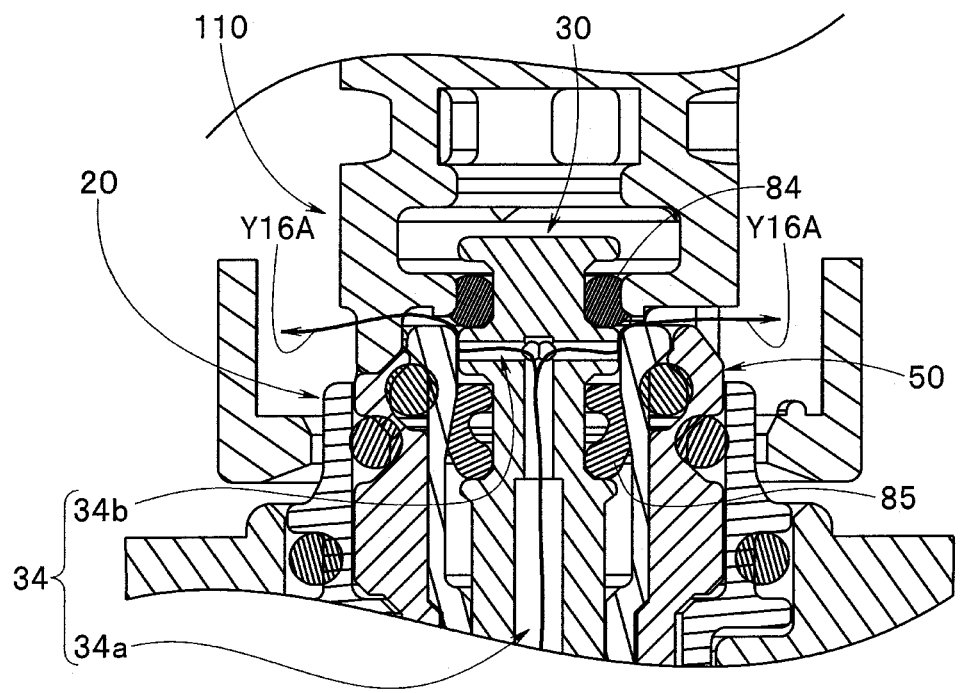
FIG. 16A is a view explaining a relationship between the vent hole and an outside at a time of the pipe sleeve control unit being rotated 120 degrees to be fitted to the vent pipe sleeve.
Figure 16B:
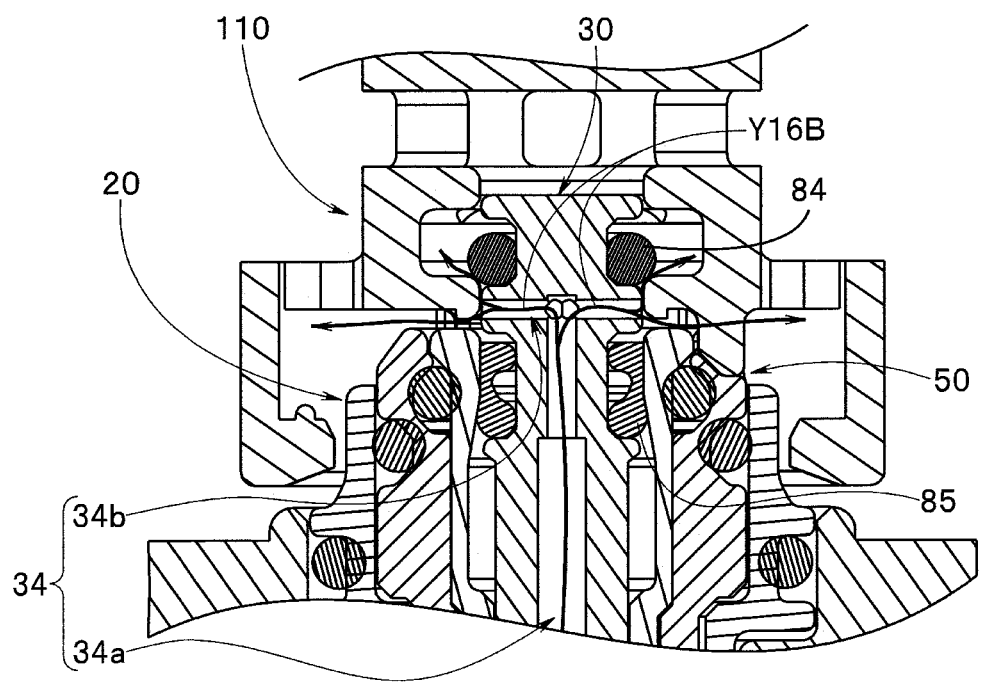
FIG. 16B is a view explaining a relationship between the vent hole and the outside at a time of the pipe sleeve control unit being rotated 180 degrees to be fitted to the vent pipe sleeve.

In the pipe sleeve control unit 110 of the present embodiment, the fitting operation is performed by causing the pipe sleeve control unit 110 to rotate in the direction shown by the arrow Y12B in FIG. 12B. At this time, in a period from the 120 degrees rotation state illustrated in FIG. 16A to the 180 degrees rotation state illustrated in FIG. 16B, for example, the vent openings 33m of the vent hole 34 and the outside communicate with each other as shown by arrows Y16A and Y16B. In other words, the outside and the connector space 16S communicate with each other by the vent hole 34.

Figure 16C:
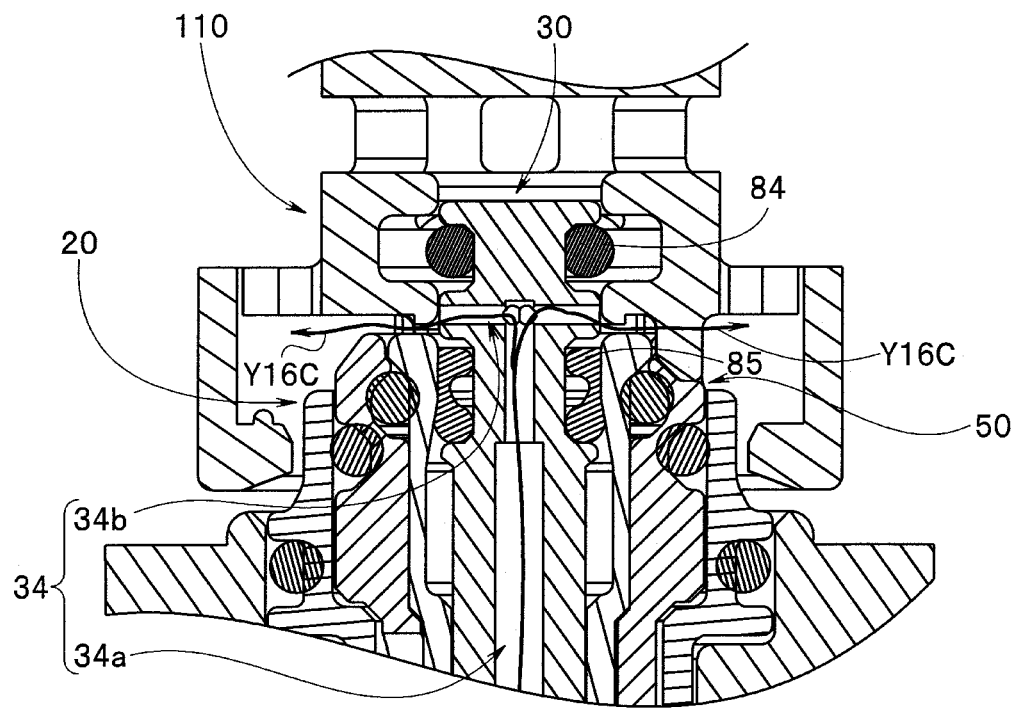
FIG. 16C is a view explaining a relationship between the vent hole and the outside at a time of the pipe sleeve control unit being rotated 90 degrees to be detached from the vent pipe sleeve after completion of fitting.
Figure 16D:
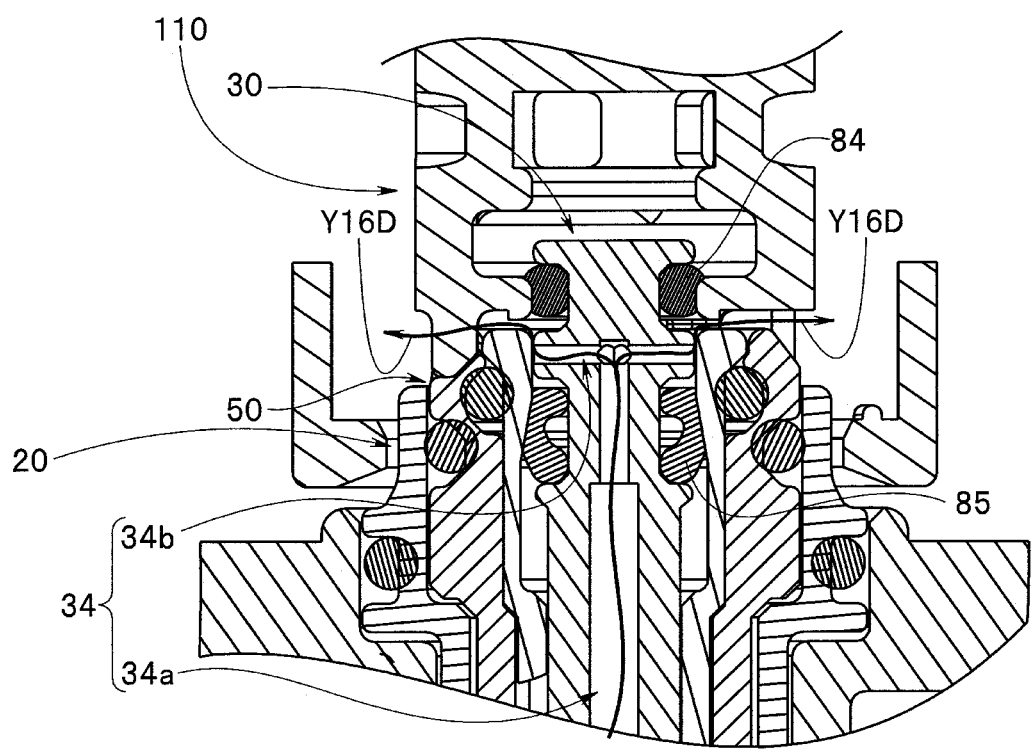
FIG. 16D is a view explaining a relationship between the vent hole and the outside at a time of the pipe sleeve control unit being rotated by 150 degrees to be detached from the vent pipe sleeve after completion of fitting.

After fitting is completed, the pipe sleeve control unit 110 is rotated from 270 degrees to 0 degrees in an opposite direction to the aforementioned arrow Y12B to perform detachment. At this time, in a period from a state of the pipe sleeve control unit 110 being rotated 90 degrees in the opposite direction illustrated in FIG. 16C to a state of the pipe sleeve control unit 110 being rotated 150 degrees in the opposite direction illustrated in FIG. 16D, the vent openings 33m of the vent hole 34 and the outside communicate with each other as shown by arrows Y16C and Y16D similarly to the above.

Note that though not illustrated, during fitting, watertightness of the fourth O-shaped ring 84 or the fifth O-shaped ring 85 is in an incomplete state in the period from the rotation angle of 60 degrees to 210 degrees. During detachment, the watertightness of the fourth O-shaped ring 84 or the fifth O-shaped ring 85 is also in an incomplete state in the time period in which the rotation angle is 60 degrees to 210 degrees in the opposite direction, similarly to the above.

Accordingly, while the pipe sleeve control unit 110 is caused to rotate to fit the adaptor 10 to the vent pipe sleeve 20 as described above, the inside of the connector space 16S and the outside communicate with each other temporarily and the pressure in the connector space 16S and atmospheric pressure become uniform.

When the adaptor 10 is detached from the vent pipe sleeve 20 after sterilization processing is finished, the inside of the connector space 16S and the outside communicate with each other temporarily, and negative pressure at the time of sterilization is released.

Accordingly, it is possible to make an open valve unnecessary in the endoscope connector 16 of the present embodiment and realize compactification of the endoscope connector 16.

When the adaptor is formed by attaching a water leakage checker to the pipe sleeve control unit 110 fitted to the vent pipe sleeve 20 in place of the check valve unit 100, it is possible to perform water leakage check by supplying air from the water leakage checker.

The present invention is not limited to the aforementioned embodiment, and various changes or applications can be made within the range without departing from the gist of the invention.

What is claimed is:

1. A vent control valve for an endoscope comprising:
   a shaft body including a pin fixing portion which is provided in an outer peripheral surface and to which one end of a cam pin is fixed, and a vent hole including a long hole set to a predetermined depth with an opening provided in one end surface, and a long hole communication hole including a vent opening formed in the outer peripheral surface and configured to cause an outside and an inside of the long hole to communicate with each other through the vent opening;
   a tubular member including a shaft body hole that is a through-hole configured to house the shaft body rotatably around an axis and movably in an axial direction and extending in a longitudinal direction along a center axis, and a cam groove in which another end portion of the cam pin is slidably disposed, on an outer peripheral portion;
   a rotational member including a tubular member hole where the tubular member is disposed rotatably around an axis, an elongated cam pin groove where the other end portion of the cam pin protruded outward from the cam groove is disposed, the cam pin groove extending in a longitudinal direction along a center axis from one end surface and causing the tubular member hole and an outside to communicate with each other, and a plurality of engaging holes provided at predetermined positions of another end surface; and
   a cylindrical housing member including an attaching portion fixedly provided in a casing through-hole causing an internal space of a casing configuring the endoscope and an outside to communicate with each other, and a housing hole including a bottom surface opening of a housing through-hole communicating with the internal space, in a bottom surface, and configured to house the rotational member.

2. The vent control valve for an endoscope according to claim 1, wherein the housing member further includes a plurality of protruding portions protruded from a peripheral end portion of the attaching portion.

3. The vent control valve for an endoscope according to claim 1, further comprising:
   a first watertight member configured to maintain watertightness between an outer peripheral surface of an adaptor attaching portion of the housing member, and an inner peripheral surface of a watertightness maintaining hole of the through-hole;
   a second watertight member configured to maintain watertightness between an outer peripheral surface of a rotational main body of the rotational member, and a main body housing hole of the housing hole;
   a third watertight member configured to maintain watertightness between an inner peripheral surface of a main body portion hole of the rotational member, and an outer peripheral surface of a main body portion of the tubular member; and
   a fourth watertight member and a fifth watertight member disposed in predetermined positions between an inner peripheral surface of a watertightness maintaining portion of the tubular member and an outer peripheral surface of a large diameter portion of the shaft body, and configured to maintain watertightness.

4. The vent control valve for an endoscope according to claim 3, wherein the other end portion of the cam pin with the one end fixedly provided at the shaft body is moved along the cam pin groove while being slid in the cam groove with rotation of the rotational member in a clockwise direction or in a counterclockwise direction, and the shaft body moves in an axial direction of the casing through-hole.

5. The vent control valve for an endoscope according to claim 4, wherein the rotational member is rotated from an initial position to a first angle, and the shaft body moves between a first position and a second position separated in an axial direction.

6. The vent control valve for an endoscope according to claim 5, wherein
   the shaft body in the first position maintains watertightness between the inner peripheral surface of the watertightness maintaining portion of the tubular member and the outer peripheral surface of the large diameter portion of the shaft body by the fourth watertight member, and
   the shaft body in the second position is in a state where a part of the fifth watertight member protrudes to an outside, and a remaining part maintains watertightness between the inner peripheral surface of the watertightness maintaining portion of the tubular member and the outer peripheral surface of the large diameter portion of the shaft body.

7. The vent control valve for an endoscope according to claim 5, wherein
   until a watertight member configured to maintain watertightness between the inner peripheral surface of the watertightness maintaining portion of the tubular member and the outer peripheral surface of the large diameter portion of the shaft body is switched from the fourth watertight member to the fifth watertight member, or until the watertight member is switched from the fifth watertight member to the fourth watertight member, and
   the vent opening is exposed to an outside, and the outside and the internal space communicate with each other by the vent hole.

8. An endoscope comprising a vent control valve, wherein the vent control valve comprises:
   a shaft body including a pin fixing portion which is provided in an outer peripheral surface and to which one end of a cam pin is fixed, and a vent hole including a long hole set to a predetermined depth with an opening provided in one end surface and a long hole communication hole including a vent opening formed in the outer peripheral surface and configured to cause an outside and an inside of the long hole to communicate with each other through the vent opening;
   a tubular member including a shaft body hole that is a through-hole configured to house the shaft body rotatably around an axis and movably in an axial direction and extending in a longitudinal direction along a center axis, and a cam groove in which another end portion of the cam pin is slidably disposed, on an outer peripheral portion;

a rotational member including a tubular member hole where the tubular member is disposed rotatably around an axis, an elongated cam pin groove where the other end portion of the cam pin protruded outward from the cam groove is disposed, the cam pin groove extending in a longitudinal direction along a center axis from one end surface and causing the tubular member hole and an outside to communicate with each other, and a plurality of engaging holes provided at predetermined positions of another end surface; and a cylindrical housing member including an attaching portion fixedly provided in a casing through-hole causing an internal space of a casing configuring the endoscope and an outside to communicate with each other, and a housing hole including a bottom surface opening of a housing through-hole communicating with the internal space, in a bottom surface, and configured to house the rotational member.

9. An endoscope comprising:

the vent control valve for an endoscope according to claim 3; and a pipe sleeve control unit comprising locking portions engaging with the plurality of engaging holes disposed in the rotational member, and a housing space where a fourth ring housing portion where the fourth watertight member provided on the large diameter portion of the shaft body is disposed in close contact, a fifth ring housing portion where the fifth watertight member is disposed in close contact, and a boundary surface housing portion where a boundary surface is disposed are disposed.

* * * * *